(12) United States Patent
Tournier-Lasserve et al.

(10) Patent No.: US 6,537,775 B1
(45) Date of Patent: Mar. 25, 2003

(54) GENE INVOLVED IN CADASIL, METHOD OF DIAGNOSIS AND THERAPEUTIC APPLICATION

(75) Inventors: Elisabeth Tournier-Lasserve, Paris (FR); Anne Joutel, Paris (FR); Marie-Germaine Bousser, Paris (FR); Jean-François Bach, Paris (FR)

(73) Assignees: Institut National de la Sante et de la Recherche (INSERM), Paris (FR); Assistance Publique - Hopitaux de Paris, Paris (FR)

( * ) Notice: Subject to any disclaimer, the term of this patent is extended or adjusted under 35 U.S.C. 154(b) by 0 days.

(21) Appl. No.: 09/230,652

(22) PCT Filed: Jul. 31, 1997

(86) PCT No.: PCT/FR97/01433

§ 371 (c)(1), (2), (4) Date: May 17, 1999

(87) PCT Pub. No.: WO98/05775

PCT Pub. Date: Feb. 12, 1998

(30) Foreign Application Priority Data

Aug. 1, 1996 (FR) .............................................. 96 09733
Apr. 16, 1997 (FR) .............................................. 97 04680

(51) Int. Cl.[7] .......................... C07H 21/04; C12P 21/06; C12N 15/00; C12N 1/20
(52) U.S. Cl. ..................... 435/69.1; 435/71.1; 435/71.2; 435/320.1; 435/325; 435/252.3; 435/254.11; 435/257.2; 435/440; 536/23.5
(58) Field of Search ............................ 536/23.1, 23.4, 536/23.5; 435/69.1, 71.1, 346, 252.3, 320.1, 71.2, 325, 254.11, 257.2, 440; 530/350

(56) References Cited

FOREIGN PATENT DOCUMENTS

CA 2116628 2/1994

OTHER PUBLICATIONS

Sambrook et al Molecular Cloning, A Laboratory Manual, 2nd, 16.1–16.81, 1989.*
Rudinger et al., in "Peptide Hormones", edited by Parsons, J.A., University Park Press, Jun. 1976, p. 6.*
Burgess et al., The Journal of Cell Biology, 111:2129–2138, 1990.*
Lardelli et al., "The Novel Notch Homologue Mouse Notch 3 Lacks specific Epidermal Growth Factor–Repeats and is Expressed in Proliferating Neuroepithelium", Mech. of Develop., 46:123–136 (1994).
Lindsell et al., "Expression Patterns of Jagged, Delta1, Notch1, Notch2, and Notch3 Genes Identify Ligand–Receptor Pairs that may Function in Neural Development", Mole. and Cell. Neuroscience, 8:14–27 (1996).
Ducros et al., "Cerebral Autosomal Dominant Arteriopathy with Subcortical Infarcts and Leukoencephalopathy, Genetic Homogeneity, and Mapping of The Locus Within a 2–cM Interval", A.m. J. Hum. Genet., 58:171–181 (1996).
Joutel et al., "Notch3 Mutations in Cadasil, A Hereditary Adult–Onset Condition Causing Stroke and Dementia", Nature, 383:707–710.
Lardelli et al., "Expression of the Notch 3 intracellular Domain in Mouse Central Nervous System Progenitor Cells is Lethal and Leads to Disturbed Neural tube Development", Mech. of Develop., 59:177–190.
Ophoff et al., "Gene For Familial Hemiplegic Migraine on Chromosome 19p13", Posters: Molecular Etiology of Disease, vol. 57, No. 4, pp. A222, Abstract 1284 (1995).
Joutel et al., "Identification of Expressed Sequences from the Cadasil Region ON 19p", Amer. J. of Human Genet., vol. 57, No. 3, pp. A342, Abstract 1985 (1995).
Joutel et al., "Identification of the Cadasil Gene", Stroke, vol. 28, No. 1, pp. 246, Abstract 65 (1997).
C. Larsson et al., "The Human NOTCH1, 2, and 3 Genes Are Located at Chromosome Positions 9q34, 1p13–p11, and 19p.13.2–p13.1 in Regions of Neoplasia–Associated Translocation," Genomics, vol. 24, No. 2, pp. 253–258 (1994).

* cited by examiner

Primary Examiner—Patricia A. Duffy
(74) Attorney, Agent, or Firm—Finnegan, Henderson, Farabow, Garrett & Dunner, LLP

(57) ABSTRACT

The invention concerns the Notch3 gene and the corresponding protein, which are involved in CADASIL. The invention concerns, in particular, methods for demonstrating mutations in this gene, which are linked to the risk of developing CADASIL. The invention also concerns models and products for treating CADASIL and related diseases.

12 Claims, 11 Drawing Sheets

Figures 2A, 2B:
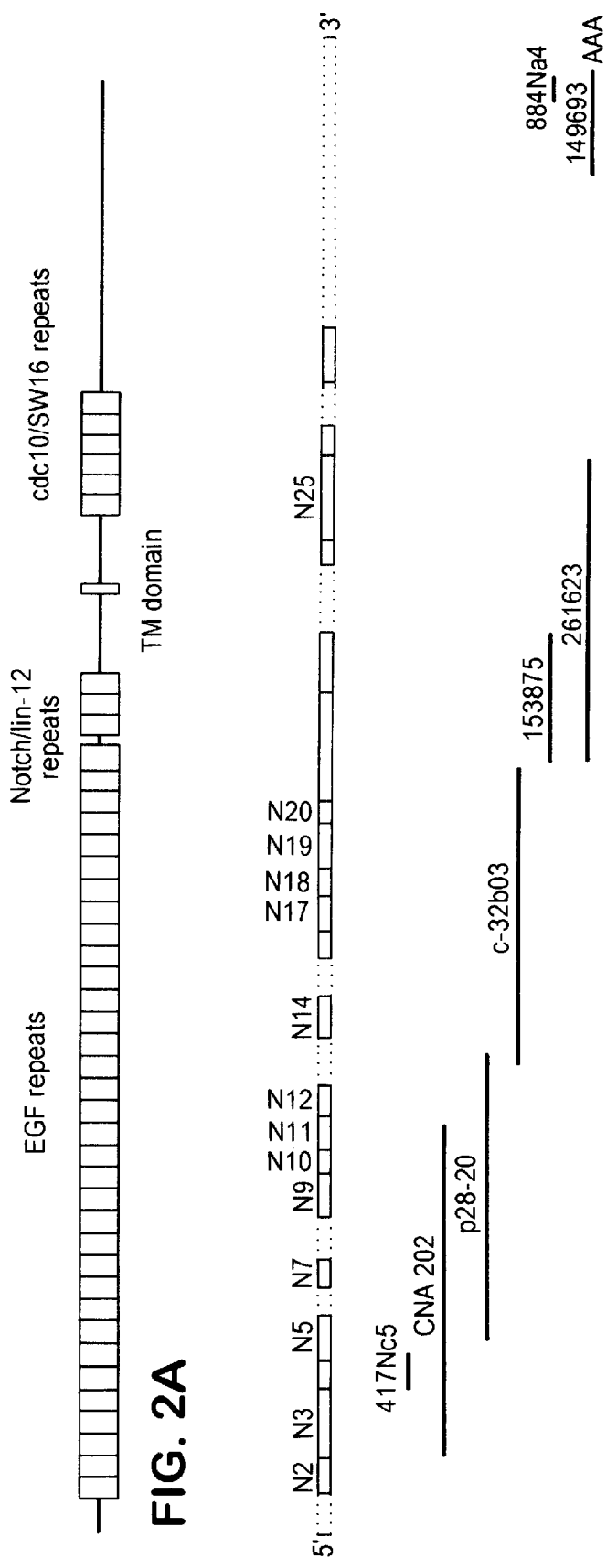

```
              2                        17                        32
ACG CGG CGC GGA GGC TGG CCC GGG ACG CGC CCG GAG CCC AGG GAA
       47                      62                       77
GGA GGG AGG AGG GGA GGG TCG CGG CCG GCC GCC ATG GGG CCG GGG
                                                 M   G   P   G
        92                       107                      122
GCC CGT GGC CGC CGC CGC CGC CGT CGC CCG ATG TCG CCG CCA CCG
 A   R   G   R   R   R   R   R   R   P   M   S   P   P   P
       137                      152                      167
CCA CCG CCA CCC GTG CGG GCG CTG CCC CTG CTG CTG CTG CTA GCG
 P   P   P   P   V   R   A   L   P   L   L   L   L   L   A
       182                      197                      212
GGG CCG GGG GCT GCA GCC CCC CCT TGC CTG GAC GGA AGC CCG TGT
 G   P   G   A   A   A   P   P   C   L   D   G   S   P   C
       227                      242                      257
GCA AAT GGA GGT CGT TGC ACC CAG CTG CCC TCC CGG GAG GCT GCC
 A   N   G   G   R   C   T   Q   L   P   S   R   E   A   A
       272                      287                      302
TGC CTG TGC CCG CCT GGC TGG GTG GGT GAG CGG TGT CAG CTG GAG
 C   L   C   P   P   G   W   V   G   E   R   C   Q   L   E
       317                      332                      347
GAC CCC TGT CAC TCA GGC CCC TGT GCT GGC CGT GGT GTC TGC CAG
 D   P   C   H   S   G   P   C   A   G   R   G   V   C   Q
       362                      377                      392
AGT TCA GTG GTG GCT GGC ACC GCC CGA TTC TCA TGC CGG TGC CCC
 S   S   V   V   A   G   T   A   R   F   S   C   R   C   P
       407                      422                      437
CGT GGC TTC CGA GGC CCT GAC TGC TCC CTG CCA GAT CCC TGC CTC
 R   G   F   R   G   P   D   C   S   L   P   D   P   C   L
       452                      467                      482
AGC AGC CCT TGT GCC CAC GGT GCC CGC TGC TCA GTG GGG CCC GAT
 S   S   P   C   A   H   G   A   R   C   S   V   G   P   D
       497                      512                      527
GGA CGC TTC CTC TGC TCC TGC CCA CCT GGC TAC CAG GGC CGC AGC
 G   R   F   L   C   S   C   P   P   G   Y   Q   G   R   S
       542                      557                      572
TGC CGA AGC GAC GTG GAT GAG TGC CGG GTG GGT GAG CCC TGC CGC
 C   R   S   D   V   D   E   C   R   V   G   E   P   C   R
       587                      602                      617
CAT GGT GGC ACC TGC CTC AAC ACA CCT GGC TCC TTC CGC TGC CAG
 H   G   G   T   C   L   N   T   P   G   S   F   R   C   Q
       632                      647                      662
TGT CCA GCT GGC TAC ACA GGG CCA CTA TGT GAG AAC CCC GCG GTG
 C   P   A   G   Y   T   G   P   L   C   E   N   P   A   V
       677                      692                      707
CCC TGT GCG CCC TCA CCA TGC CGT AAC GGG GGC ACC TGC AGG CAG
 P   C   A   P   S   P   C   R   N   G   G   T   C   R   Q
       722                      737                      752
AGT GGC GAC CTC ACT TAC GAC TGT GCC TGT CTT CCT GGG TTT GAG
 S   G   D   L   T   Y   D   C   A   C   L   P   G   F   E
       767                      782                      797
GGT CAG AAT TGT GAA GTG AAC GTG GAC GAC TGT CCA GGA CAC CGA
 G   Q   N   C   E   V   N   V   D   D   C   P   G   H   R
       812                      827                      842
TGT CTC AAT GGG GGA ACA TGC GTG GAT GGC GTC AAC ACC TAT AAC
 C   L   N   G   G   T   C   V   D   G   V   N   T   Y   N
       857                      872                      887
TGC CAG TGC CCT CCT GAG TGG ACA GGC CAG TTC TGC ACG GAG GAC
 C   Q   C   P   P   E   W   T   G   Q   F   C   T   E   D
       902                      917                      932
GTG GAT GAG TGT CAG CTG CAG CCC AAC GCC TGC CAC AAT GGG GGT
 V   D   E   C   Q   L   Q   P   N   A   C   H   N   G   G
       947                      962                      977
ACC TGC TTC AAC ACG CTG GGT GGC CAC AGC TGC GTG TGT GTC AAT
 T   C   F   N   T   L   G   G   H   S   C   V   C   V   N
       992                     1007                     1022
GGC TGG ACA GGT GAG AGC TGC AGT CAG AAT ATC GAT GAC TGT GCC
 G   W   T   G   E   S   C   S   Q   N   I   D   D   C   A
```

FIG. 1A

```
1037                    1052                    1067
ACA GCC GTG TGC TTC CAT GGG GCC ACC TGC CAT GAC CGC GTG GCT
 T   A   V   C   F   H   G   A   T   C   H   D   R   V   A
1082                    1097                    1112
TCT TTC TAC TGT GCC TGC CCC ATG GGC AAG ACT GGC CTC CTG TGT
 S   F   Y   C   A   C   P   M   G   K   T   G   L   L   C
1127                    1142                    1157
CAC CTG GAT GAC GCC TGT GTC AGC AAC CCC TGC CAC GAG GAT GCT
 H   L   D   D   A   C   V   S   N   P   C   H   E   D   A
1172                    1187                    1202
ATC TGT GAC ACA AAT CCG GTG AAC GGC CGG GCC ATT TGC ACC TGT
 I   C   D   T   N   P   V   N   G   R   A   I   C   T   C
1217                    1232                    1247
CCT CCC GGC TTC ACG GGT GGG GCA TGT GAC CAG GAT GTG GAC GAG
 P   P   G   F   T   G   G   A   C   D   Q   D   V   D   E
1262                    1277                    1292
TGC TCT ATC GGC GCC AAC CCC TGC GAG CAC TTG GGC AGG TGC GTG
 C   S   I   G   A   N   P   C   E   H   L   G   R   C   V
1307                    1322                    1337
AAC ACG CAG GGC TCC TTC CTG TGC CAG TGC GGT CGT GGC TAC ACT
 N   T   Q   G   S   F   L   C   Q   C   G   R   G   Y   T
1352                    1367                    1382
GGA CCT CGC TGT GAG ACC GAT GTC AAC GAG TGT CTG TCG GGG CCC
 G   P   R   C   E   T   D   V   N   E   C   L   S   G   P
1397                    1412                    1427
TGC CGA AAC CAG GCC ACG TGC CTC GAC CGC ATA GGC CAG TTC ACC
 C   R   N   Q   A   T   C   L   D   R   I   G   Q   F   T
1442                    1457                    1472
TGT ATC TGT ATG GCA GGC TTC ACA GGA ACC TAT TGC GAG GTG GAC
 C   I   C   M   A   G   F   T   G   T   Y   C   E   V   D
1487                    1502                    1517
ATT GAC GAG TGT CAG AGT AGC CCC TGT GTC AAC GGT GGG GTC TGC
 I   D   E   C   Q   S   S   P   C   V   N   G   V   C
1532                    1547                    1562
AAG GAC CGA GTC AAT GGC TTC AGC TGC ACC TGC CCC TCG GGC TTC
 K   D   R   V   N   G   F   S   C   T   C   P   S   G   F
1577                    1592                    1607
AGC GGC TCC ACG TGT CAG CTG GAC GTG GAC GAA TGC GCC AGC ACG
 S   G   S   T   C   Q   L   D   V   D   E   C   A   S   T
1622                    1637                    1652
CCC TGC AGG AAT GGC GCC AAA TGC GTG GAC CAG CCC GAT GGC TAC
 P   C   R   N   G   A   K   C   V   D   Q   P   D   G   Y
1667                    1682                    1697
GAG TGC CGC TGT GCC GAG GGC TTT GAG GGC ACG CTG TGT GAT CGC
 E   C   R   C   A   E   G   F   E   G   T   L   C   D   R
1712                    1727                    1742
AAC GTG GAC GAC TGC TCC CCT GAC CCA TGC CAC CAT GGT CGC TGC
 N   V   D   D   C   S   P   D   P   C   H   H   G   R   C
1757                    1772                    1787
GTG GAT GGC ATC GCC AGC TTC TCA TGT GCC TGT GCT CCT GGC TAC
 V   D   G   I   A   S   F   S   C   A   C   A   P   G   Y
1802                    1817                    1832
ACG GGC ACA CGC TGC GAG AGC CAG GTG GAC GAA TGC CGC AGC CAG
 T   G   T   R   C   E   S   Q   V   D   E   C   R   S   Q
1847                    1862                    1877
CCC TGC CGC CAT GGC GGC AAA TGC CTA GAC CTG GTG GAC AAG TAC
 P   C   R   H   G   G   K   C   L   D   L   V   D   K   Y
1892                    1907                    1922
CTC TGC CGC TGC CCT TCT GGG ACC ACA GGT GTG AAC TGC GAA GTG
 L   C   R   C   P   S   G   T   T   G   V   N   C   E   V
1937                    1952                    1967
AAC ATT GAC GAC TGT GCC AGC AAC CCC TGC ACC TTT GGA GTC TGC
 N   I   D   D   C   A   S   N   P   C   T   F   G   V   C
1982                    1997                    2012
CGT GAT GGC ATC AAC CGC TAC GAC TGT GTC TGC CAA CCT GGC TTC
 R   D   G   I   N   R   Y   D   C   V   C   Q   P   G   F
2027                    2042                    2057
ACA GGG CCC CTT TGT AAC GTG GAG ATC AAT GAG TGT GCT TCC AGC
 T   G   P   L   C   N   V   E   I   N   E   C   A   S   S
```

FIG. 1B

```
2072                    2087                    2102
CCA TGC GGC GAG GGA GGT TCC TGT GTG GAT GGG GAA AAT GGC TTC
 P   C   G   E   G   G   S   C   V   D   G   E   N   G   F
2117                    2132                    2147
CGC TGC CTC TGC CCG CCT GGC TCC TTG CCC CCA CTC TGC CTC CCC
 R   C   L   C   P   P   G   S   L   P   P   L   C   L   P
2162                    2177                    2192
CCG AGC CAT CCC TGT GCC CAT GAG CCC TGC AGT CAC GGC ATC TGC
 P   S   H   P   C   A   H   E   P   C   S   H   G   I   C
2207                    2222                    2237
TAT GAT GCA CCT GGC GGG TTC CGC TGT GTG TGT GAG CCT GGC TGG
 Y   D   A   P   G   G   F   R   C   V   C   E   P   G   W
2252                    2267                    2282
AGT GGC CCC CGC TGC AGC CAG AGC CTG GCC CGA GAC GCC TGT GAG
 S   G   P   R   C   S   Q   S   L   A   R   D   A   C   E
2297                    2312                    2327
TCC CAG CCG TGC AGG GCC GGT GGG ACA TGC AGC AGC GAT GGA ATG
 S   Q   P   C   R   A   G   G   T   C   S   S   D   G   M
2342                    2357                    2372
GGT TTC CAC TGC ACC TGC CCG CCT GGT GTC CAG GGA CGT CAG TGT
 G   F   H   C   T   C   P   P   G   V   Q   G   R   Q   C
2387                    2402                    2417
GAA CTC CTC TCC CCC TGC ACC CCG AAC CCC TGT GAG CAT GGG GGC
 E   L   L   S   P   C   T   P   N   P   C   E   H   G   G
2432                    2447                    2462
CGC TGC GAG TCT GCC CCT GGC CAG CTG CCT GTC TGC TCC TGC CCC
 R   C   E   S   A   P   G   Q   L   P   V   C   S   C   P
2477                    2492                    2507
CAG GGC TGG CAA GGC CCA CGA TGC CAG CAG GAT GTG GAC GAG TGT
 Q   G   W   Q   G   P   R   C   Q   Q   D   V   D   E   C
2522                    2537                    2552
GCT GGC CCC GCA CCC TGT GGC CCT CAT GGT ATC TGC ACC AAC CTG
 A   G   P   A   P   C   G   P   H   G   I   C   T   N   L
2567                    2582                    2597
GCA GGG AGT TTC AGC TGC ACC TGC CAT GGA GGG TAC ACT GGC CCT
 A   G   S   F   S   C   T   C   H   G   G   Y   T   G   P
2612                    2627                    2642
TCC TGT GAT CAG GAC ATC AAT GAC TGT GAC CCC AAC CCA TGC CTG
 S   C   D   Q   D   I   N   D   C   D   P   N   P   C   L
2657                    2672                    2687
AAC GGT GGC TCG TGC CAA GAC GGC GTG GGC TCC TTT TCC TGC TCC
 N   G   G   S   C   Q   D   G   V   G   S   F   S   C   S
2702                    2717                    1732
TGC CTC CCT GGT TTC GCC GGC CCA CGA TGC GCC CGC GAT GTG GAT
 C   L   P   G   F   A   G   P   R   C   A   R   D   V   D
2747                    2762                    2777
GAG TGC CTG AGC AAC CCC TGC GGC CCG GGC ACC TGT ACC GAC CAC
 E   C   L   S   N   P   C   G   P   G   T   C   T   D   H
2792                    2807                    2822
GTG GCC TCC TTC ACC TGC ACC TGC CCG CCG GGC TAC GGA GGC TTC
 V   A   S   F   T   C   T   C   P   P   G   Y   G   G   F
2837                    2852                    2867
CAC TGC GAA CAG GAC CTG CCC GAC TGC AGC CCC AGC TCC TGC TTC
 H   C   E   Q   D   L   P   D   C   S   P   S   S   C   F
2882                    2897                    2912
AAT GGC GGG ACC TGT GTG GAC GGC GTG AAC TCG TTC AGC TGC CTG
 N   G   G   T   C   V   D   G   V   N   S   F   S   C   L
2927                    2942                    2957
TGC CGT CCC GGC TAC ACA GGA GCC CAC TGC CAA CAT GAG GCA GAC
 C   R   P   G   Y   T   G   A   H   C   Q   H   E   A   D
2972                    2987                    3002
CCC TGC CTC TCG CGG CCC TGC CTA CAC GGG GGC GTC TGC AGC GCC
 P   C   L   S   R   P   C   L   H   G   G   V   C   S   A
3017                    3032                    3047
GCC CAC CCT GGC TTC CGC TGC ACC TGC CTC GAG AGC TTC ACG GGC
 A   H   P   G   F   R   C   T   C   L   E   S   F   T   G
3062                    3077                    3092
CCG CAG TGC CAG ACG CTG GTG GAT TGG TGC AGC CGC CAG CCT TGT
 P   Q   C   Q   T   L   V   D   W   C   S   R   Q   P   C
```

FIG. 1C

```
3107                3122                      3137
CAA AAC GGG GGT CGC TGC GTC CAG ACT GGG GCC TAT TGC CTT TGT
 Q   N   G   G   R   C   V   Q   T   G   A   Y   C   L   C
3152                3167                      3182
CCC CCT GGA TGG AGC GGA CGC CTC TGT GAC ATC CGA AGC TTG CCC
 P   P   G   W   S   G   R   L   C   D   I   R   S   L   P
3197                3212                      3227
TGC AGG GAG GCC GCA GCC CAG ATC GGG GTG CGG CTG GAG CAG CTG
 C   R   E   A   A   A   Q   I   G   V   R   L   E   Q   L
3242                3257                      3272
TGT CAG GCG GGT GGG CAG TGT GTG GAT GAA GAC AGC TCC CAC TAC
 C   Q   A   G   G   Q   C   V   D   E   D   S   S   H   Y
3287                3257                      3272
TGC GTG TGC CCA GAG GGC CGT ACT GGT AGC CAC TGT GAG CAG GAG
 C   V   C   P   E   G   R   T   G   S   H   C   E   Q   E
3332                3347                      3362
GTG GAC CCC TGC TTG GCC CAG CCC TGC CAG CAT GGG GGG ACC TGC
 V   D   P   C   L   A   Q   P   C   Q   H   G   G   T   C
3377                3392                      3407
CGT GGC TAT ATG GGG GGC TAC ATG TGT GAG TGT CTT CCT GGC TAC
 R   G   Y   M   G   G   Y   M   C   E   C   L   P   G   Y
3422                3437                      3452
AAT GGT GAT AAC TGT GAG GAC GAC GTG GAC GAG TGT GCC TCC CAG
 N   G   D   N   C   E   D   D   V   D   E   C   A   S   Q
3467                3482                      3497
CCC TGC CAG CAC GGG GGT TCA TGC ATT GAC CTC GTG GCC CGC TAT
 P   C   Q   H   G   G   S   C   I   D   L   V   A   R   Y
3512                3527                      3542
CTC TGC TCC TGT CCC CCA GGA ACG CTG GGG GTG CTC TGC GAG ATT
 L   C   S   C   P   P   G   T   L   G   V   L   C   E   I
3557                3572                      3587
AAT GAG GAT GAC TGC GGC CCA GGC CCA CCG CTG GAC TCA GGG CCC
 N   E   D   D   C   G   P   G   P   P   L   D   S   G   P
3602                3617                      3632
CGG TGC CTA CAC AAT GGC ACC TGC GTG GAC CTG GTG GGT GGT TTC
 R   C   L   H   N   G   T   C   V   D   L   V   G   G   F
3647                3662                      3672
CGC TGC ACC TGT CCC CCA GGA TAC ACT GGT TTG CGC TGC GAG GCA
 R   C   T   C   P   P   G   Y   T   G   L   R   C   E   A
3692                3707                      3722
GAC ATC AAT GAG TGT CGC TCA GGT GCC TGC CAC GCG GCA CAC ACC
 D   I   N   E   C   R   S   G   A   C   H   A   A   H   T
3737                3752                      3767
CGG GAC TGC CTG CAG GAC CCA GGC GGA GGT TTC CGT TGC CTT TGT
 R   D   C   L   Q   D   P   G   G   G   F   R   C   L   C
3782                3797                      3812
CAT GCT GGC TTC TCA GGT CCT CGC TGT CAG ACT GTC CTG TCT CCC
 H   A   G   F   S   G   P   R   C   Q   T   V   L   S   P
3827                3842                      3857
TGC GAG TCC CAG CCA TGC CAG CAT GGA GGC CAG TGC CGT CCT AGC
 C   E   S   Q   P   C   Q   H   G   G   Q   C   R   P   S
3872                3887                      3902
CCG GGT CCT GGG GGT GGG CTG ACC TTC ACC TGT CAC TGT GCC CAG
 P   G   P   G   G   G   L   T   F   T   C   H   C   A   Q
3917                3932                      3947
CCG TTC TGG GGT CCG CGT TGC GAG CGG GTG GCG CGC TCC TGC CGG
 P   F   W   G   P   R   C   E   R   V   A   R   S   C   R
3962                3977                      3992
GAG CTG CAG TGC CCG GTG GGC GTC CCA TGC CAG CAG ACG CCC CGC
 E   L   Q   C   P   V   G   V   P   C   Q   Q   T   P   R
4007                4022                      4037
GGG CCG CGC TGC GCC TGC CCC CCA GGG TTG TCG GGA CCC TCC TGC
 G   P   R   C   A   C   P   P   G   L   S   G   P   S   C
4052                4067                      4082
CGC AGC TTC CCG GGG TCG CCG CCG GGG GCC AGC AAC GCC AGC TGC
 R   S   F   P   G   S   P   P   G   A   S   N   A   S   C
4097                4112                      4127
GCG GCC GCC CCC TGT CTC CAC GGG GGC TCC TGC CGC CCC GCG CCG
 A   A   A   P   C   L   H   G   G   S   C   R   P   A   P
```

FIG. 1D

```
       4142                  4157                  4172
CTC GCG CCC TTC TTC CGC TGC GCT TGC GCG CAG GGC TGG ACC GGG
 L   A   P   F   F   R   C   A   C   A   Q   G   W   T   G
       4187                  4202                  4217
CCG CGC TGC GAG GCG CCC GCC GCG GCA CCC GAG GTC TCG GAG GAG
 P   R   C   E   A   P   A   A   A   P   E   V   S   E   E
       4232                  4247                  4262
CCG CGG TGC CCG CGC GCC GCC TGC CAG GCC AAG CGC GGG GAC CAG
 P   R   C   P   R   A   A   C   Q   A   K   R   G   D   Q
       4277                  4292                  4307
CGC TGC GAC CGC GAG TGC AAC AGC CCA GGC TGC GGC TGG GAC GGC
 R   C   D   R   E   C   N   S   P   G   C   G   W   D   G
       4322                  4337                  4352
GGC GAC TGC TCG CTG AGC GTG GGC GAC CCC TGG CGG CAA TGC GAG
 G   D   C   S   L   S   V   G   D   P   W   R   Q   C   E
       4367                  4382                  4397
GCG CTG CAG TGC TGG CGC CTC TTC AAC AAC AGC CGC TGC GAC CCC
 A   L   Q   C   W   R   L   F   N   N   S   R   C   D   P
       4412                  4427                  4442
GCC TGC AGC TCG CCC GCC TGC CTC TAC GAC AAC TTC GAC TGC CAC
 A   C   S   S   P   A   C   L   Y   D   N   F   D   C   H
       4457                  4472                  4487
GCC GGT GGC CGC GAG CGC ACT TGC AAC CCG GTG TAC GAG AAG TAC
 A   G   G   R   E   R   T   C   N   P   V   Y   E   K   Y
       4502                  4517                  4532
TGC GCC GAC CAC TTT GCC GAC GGC CGC TGC GAC CAG GGC TGC AAC
 C   A   D   H   F   A   D   G   R   C   D   Q   G   C   N
       4547                  4562                  4577
ACG GAG GAG TGC GGC TGG GAT GGG CTG GAT TGT GCC AGC GAG GTG
 T   E   E   C   G   W   D   G   L   D   C   A   S   E   V
       4592                  4607                  4622
CCG GCC CTG CTG GCC CGC GGC GTG CTG GTG CTC ACA GTG CTG CTG
 P   A   L   L   A   R   G   V   L   V   L   T   V   L   L
       4637                  4652                  4667
CCG CCG GAG GAG CTA CTG CGT TCC AGC GCC GAC TTT CTG CAG CGG
 P   P   E   E   L   L   R   S   S   A   D   F   L   Q   R
       4682                  4697                  4712
CTC AGC GCC ATC CTG CGC ACC TCG CTG CGC TTC CGC CTG GAC GCG
 L   S   A   I   L   R   T   S   L   R   F   R   L   D   A
       4727                  4742                  4757
CAC GGC CAG GCC ATG GTC TTC CCT TAC CAC CGG CCT AGT CCT GGC
 H   G   Q   A   M   V   F   P   Y   H   R   P   S   P   G
       4772                  4787                  4802
TCC GAA CCC CGG GCC CGT CGG GAG CTG GCC CCC GAG GTG ATC GGC
 S   E   P   R   A   R   R   E   L   A   P   E   V   I   G
       4817                  4832                  4847
TCG GTA GTA ATG CTG GAG ATT GAC AAC CGG CTC TGC CTG CAG TCG
 S   V   V   M   L   E   I   D   N   R   L   C   L   Q   S
       4862                  4877                  4892
CCT GAG AAT GAT CAC TGC TTC CCC GAT GCC CAG AGC GCC GCT GAC
 P   E   N   D   H   C   F   P   D   A   Q   S   A   A   D
       4907                  4922                  4937
TAC CTG GGA GCG TTG TCA GCG GTG GAG CGC CTG GAC TTC CCG TAC
 Y   L   G   A   L   S   A   V   E   R   L   D   F   P   Y
       4952                  4967                  4982
CCA CTG CGG GAC GTG CGG GGG GAG CCG CTG GAG CCT CCA GAA CCC
 P   L   R   D   V   R   G   E   P   L   E   P   P   E   P
       4997                  5012                  5027
AGC GTC CCG CTG CTG CCA CTG CTA GTG GCG GGC GCT GTC TTG CTG
 S   V   P   L   L   P   L   L   V   A   G   A   V   L   L
       5042                  5057                  5072
CTG GTC ATT CTC GTC CTG GGT GTC ATG GTG GCC CGG CGC AAG CGC
 L   V   I   L   V   L   G   V   M   V   A   R   R   K   R
       5087                  5102                  5117
GAG CAC AGC ACC CTC TGG TTC CCT GAG GGC TTC TCA CTG CAC AAG
 E   H   S   T   L   W   F   P   E   G   F   S   L   H   K
       5132                  5147                  5162
GAC GTG GCC TCT GGT CAC AAG GGC CGG CGG GAA CCC GTG GGC CAG
 D   V   A   S   G   H   K   G   R   R   E   P   V   G   Q
```

FIG. 1E

```
       5177                    5192                    5207
GAC GCG CTG GGC ATG AAG AAC ATG GCC AAG GGT GAG AGC CTG ATG
 D   A   L   G   M   K   N   M   A   K   G   E   S   L   M
5222                    5237                    5252
GGG GAG GTG GCC ACA GAC TGG ATG GAC ACA GAG TGC CCA GAG GCC
 G   E   V   A   T   D   W   M   D   T   E   C   P   E   A
5267                    5282                    5297
AAG CGG CTA AAG GTA GAG GAG CCA GGC ATG GGG GCT GAG GAG GCT
 K   R   L   K   V   E   E   P   G   M   G   A   E   E   A
5312                    5327                    5342
GTG GAT TGC CGT CAG TGG ACT CAA CAC CAT CTG GTT GCT GCT GAC
 V   D   C   R   Q   W   T   Q   H   H   L   V   A   A   D
5357                    5372                    5387
ATC CGC GTG GCA CCA GCC ATG GCA CTG ACA CCA CCA CAG GGC GAC
 I   R   V   A   P   A   M   A   L   T   P   P   Q   G   D
5402                    5417                    5432
GCA GAT GCT GAT GGC ATG GAT GTC AAT GTG CGT GGC CCA GAT GGC
 A   D   A   D   G   M   D   V   N   V   R   G   P   D   G
5447                    5462                    5477
TTC ACC CCG CTA ATG CTG GCT TCC TTC TGT GGG GGG GCT CTG GAG
 F   T   P   L   M   L   A   S   F   C   G   G   A   L   E
5492                    5507                    5522
CCA ATG CCA ACT GAA GAG GAT GAG GCA GAT GAC ACA TCA GCT AGC
 P   M   P   T   E   E   D   E   A   D   D   T   S   A   S
5537                    5552                    5567
ATC ATC TCC GAC CTG ATC TGC CAG GGG GCT CAG CTT GGG GCA CGG
 I   I   S   D   L   I   C   Q   G   A   Q   L   G   A   R
5582                    5597                    5612
ACT GAC CGT ACT GGC GAG ACT GCT TTG CAC CTG GCT GCC CGT TAT
 T   D   R   T   G   E   T   A   L   H   L   A   A   R   Y
5627                    5642                    5657
GCC CGT GCT GAT GCA GCC AAG CGG CTG CTG GAT GCT GGG GCA GAC
 A   R   A   D   A   A   K   R   L   L   D   A   G   A   D
5672                    5687                    5702
ACC AAT GCC CAG GAC CAC TCA GGC CGC ACT CCC CTG CAC ACA GCT
 T   N   A   Q   D   H   S   G   R   T   P   L   H   T   A
5717                    5732                    5747
GTC ACA GCC GAT GCC CAG GGT GTC TTC CAG ATT CTC ATC CGA AAC
 V   T   A   D   A   Q   G   V   F   Q   I   L   I   R   N
5762                    5777                    5792
CGC TCT ACA GAC TTG GAT GCC CGC ATG GCA GAT GGC TCA ACG GCA
 R   S   T   D   L   D   A   R   M   A   D   G   S   T   A
5807                    5822                    5837
CTG ATC CTG GCG GCC CGC CTG GCA GTA GAG GGC ATG GTG GAA GAG
 L   I   L   A   A   R   L   A   V   E   G   M   V   E   E
5852                    5867                    5882
CTC ATC GCC AGC CAT GCT GAT GTC AAT GCT GTG GAT GAG CTT GGG
 L   I   A   S   H   A   D   V   N   A   V   D   E   L   G
5897                    5912                    5927
AAA TCA GCC TTA CAC TGG GCT GCG GCT GTG AAC AAC GTG GAA GCC
 K   S   A   L   H   W   A   A   A   V   N   N   V   E   A
5942                    5957                    5972
ACT TTG GCC CTG CTC AAA AAT GGA GCC AAT AAG GAC ATG CAG GAT
 T   L   A   L   L   K   N   G   A   N   K   D   M   Q   D
5987                    6002                    6017
AGC AAG GAG GAG ACC CCC CTA TTC CTG GCC GCC CGC GAG GGC AGC
 S   K   E   E   T   P   L   F   L   A   A   R   E   G   S
6032                    6047                    6062
TAT GAG GCT GCC AAG CTG CTG TTG GAC CAC TTT GCC AAC CGT GAG
 Y   E   A   A   K   L   L   L   D   H   F   A   N   R   E
6077                    6092                    6107
ATC ACC GAC CAC CTG GAC AGG CTG CCG CGG GAC GTA GCC CAG GAG
 I   T   D   H   L   D   R   L   P   R   D   V   A   Q   E
6122                    6137                    6152
AGA CTG CAC CAG GAC ATC GTG CGC TTG CTG GAT CAA CCC AGT GGG
 R   L   H   Q   D   I   V   R   L   L   D   Q   P   S   G
6167                    6182                    6197
CCC CGC AGC CCC CCC GGT CCC CAC GGC CTG GGG CCT CTG CTC TGT
 P   R   S   P   P   G   P   H   G   L   G   P   L   L   C
```

FIG. 1F

```
                6212                       6227                       6242
                CCT CCA GGG GCC TTC CTC CCT GGC CTC AAA GCG GCA CAG TCG GGG
                 P   P   G   A   F   L   P   G   L   K   A   A   Q   S   G
                6257                       6272                       6287
                TCC AAG AAG AGC AGG AGG CCC CCC GGG AAG GCG GGG CTG GGG CCG
                 S   K   K   S   R   R   P   P   G   K   A   G   L   G   P
                6302                       6317                       6332
                CAG GGG CCC CGG GGG CGG GGC AAG AAG CTG ACG CTG GCC TGC CCG
                 Q   G   P   R   G   R   G   K   K   L   T   L   A   C   P
                6347                       6362                       6377
                GGC CCC CTG GCT GAC AGC TCG GTC ACG CTG TCG CCC GTG GAC TCG
                 G   P   L   A   D   S   S   V   T   L   S   P   V   D   S
                6392                       6407                       6422
                CTG GAC TCC CCG CGG CCT TTC GGT GGG CCC CCT GCT TCC CCT GGT
                 L   D   S   P   R   P   F   G   G   P   P   A   S   P   G
                6437                       6452                       6467
                GGC TTC CCC CTT GAG GGG CCC TAT GCA GCT GCC ACT GCC ACT GCA
                 G   F   P   L   E   G   P   Y   A   A   A   T   A   T   A
                6482                       6497                       6512
                GTG TCT CTG GCA CAG CTT GGT GGC CCA GGC CGG GCA GGT CTA GGG
                 V   S   L   A   Q   L   G   G   P   G   R   A   G   L   G
                6527                       6542                       6557
                CGC CAG CCC CCT GGA GGA TGT GTA CTC AGC CTG GGC CTG CTG AAC
                 R   Q   P   P   G   G   C   V   L   S   L   G   L   L   N
                6572                       6587                       6602
                CCT GTG GCT GTG CCC CTC GAT TGG GCC CGG CTG CCC CCA CCT GCC
                 P   V   A   V   P   L   D   W   A   R   L   P   P   P   A
                6617                       6632                       6647
                CCT CCA GGC CCC TCG TTC CTG CTG CCA CTG GCG CCG GGA CCC CAG
                 P   P   G   P   S   F   L   L   P   L   A   P   G   P   Q
                6662                       6677                       6692
                CTG CTC AAC CCA GGG ACC CCC GTC TCC CCG CAG GAG CGG CCC CCG
                 L   L   N   P   G   T   P   V   S   P   Q   E   R   P   P
                6707                       6722                       6737
                CCT TAC CTG GCA GTC CCA GGA CAT GGC GAG GAG TAC CCG GTG GCT
                 P   Y   L   A   V   P   G   H   G   E   E   Y   P   V   A
                6752                       6767                       6782
                GGG GCA CAC AGC AGC CCC CCA AAG GCC CGC TTC CTG CGG GTT CCC
                 G   A   H   S   S   P   P   K   A   R   F   L   R   V   P
                6797                       6812                       6827
                AGT GAG CAC CCT TAC CTG ACC CCA TCC CCC GAA TCC CCT GAG CAC
                 S   E   H   P   Y   L   T   P   S   P   E   S   P   E   H
                6842                       6857                       6872
                TGG GCC AGC CCC TCA CCT CCC TCC CTC TCA GAC TGG TCC GAA TCC
                 W   A   S   P   S   P   P   S   L   S   D   W   S   E   S
                6887                       6902                       6917
                ACG CCT AGC CCA GCC ACT GCC ACT GGG GCC ATG GCC ACC ACC ACT
                 T   P   S   P   A   T   A   T   G   A   M   A   T   T   T
                6932                       6947                       6962
                GGG GCA CTG CCT GCC CAG CCA CTT CCC TTG TCT GTT CCC AGC TCC
                 G   A   L   P   A   Q   P   L   P   L   S   V   P   S   S
                6977                       6992                       7007
                CTT GCT CAG GCC CAG ACC CAG CTG GGG CCC CAG CCG GAA GTT ACC
                 L   A   Q   A   Q   T   Q   L   G   P   Q   P   E   V   T
                7022                       7037                       7052
                CCC AAG AGG CAA GTG TTG GCC TGA GAC GCT CGT CAG TTC TTA GAT
                 P   K   R   Q   V   L   A   *                    (SEQ ID NO:2)
                7067                       7082                       7097
                CTT GGG GGC CTA AAG AGA CCC CCG TCC TGC CTC CTT TCT TTC TCT 7112                       7127                       7142
                GTC TCT TCC TTC CTT TTA GTC TTT TTC ATC CTC TTC TCT TTC CAC 7157                       7172                       7187
                CAA CCC TCC TGC ATC CTT GCC TTG CAG CGT GAC CGA GAT AGG TCA 7202                       7217                       7232
                TCA GCC CAG GGC TTC AGT CTT CCT TTA TTT ATA ATG GGT GGG GGC 7247                       7262                       7277
                                       FIG. 1G
```

```
     TAC CAC CCA CCC TCT CAG TCT TGT GAA GAG TCT GGG ACC TCC TTC 7292            7307            7322
     TTC CCC ACT TCT CTC TTC CCT CAT TCC TTT CTC TCT CCT TCT GGC 7337            7352            7367
     CTC TCA TTT CCT TAC ACT CTG ACA TGA ATG AAT TAT TAT TAT TTT 7382            7397            7412
     TCT TTT TCT TTT TTT TTT TAC ATT TTG TAT AGA AAC AAA TTC ATT 7427            7442            7457
     TAA ACA AAC TTA TTA TTA TTA TTT TTT ACA AAA TAT ATA TAT GGA 7472            7487            7502
     GAT GCT CCC TCC CCC TGT GAA CCC CCC AGT GCC CCC GTG GGG CTG 7517            7532            7547
     AGT CTG TGG GCC CAT TCG GCC AAG CTG GAT TCT GTG TAC CTA GTA 7562            7577            7592
     CAC AGG CAT GAC TGG GAT CCC GTG TAC CGA GTA CAC GAC CCA GGT 7607            7622            7637
     ATG TAC CAA GTA GGC ACC CTT GGG CGC ACC CAC TGG GGC CAG GGG 7652            7667            7682
     TCG GGG GAG TGT TGG GAG CCT CCT CCC CAC CCC ACC TCC CTC ACT 7697            7712            7727
     TCA CTG CAT TCC AGA TTG GAC ATG TTC CAT AGC CTT GCT GGG GAA 7742            7757            7772
     GGG CCC ACT GCC AAC TCC CTC TGC CCC AGC CCC ACC CTT GGC CAT 7787            7802            7817
     CTC CCT TTG GGA ACT AGG GGG CTG CTG GTG GGA AAT GGG AGC CAG 7832            7847            7862
     GGC AGA TGT ATG CAT TCC TTT ATG TCC CTG TAA ATG TGG GAC TAC 7877            7892            7907
     AAG AAG AGG AGC TGC CTG AGT GGT ACT TTC TCT TCC TGG TAA TCC 7922            7937            7952
     TCT GGC CCA GCC TTA TGG CAG AAT AGA GGT ATT TTT AGG CTA TTT 7967            7982            7997
     TTG TAA TAT GGC TTC TGG TCA AAA TCC CTG TGT AGC TGA ATT CCC 8012            8027            8042
     AAG CCC TGC ATT GTA CAG CCC CCC ACT CCC CTC ACC ACC TAA TAA 8057            8072
     AGG AAT AGT AAA CAC TCA AAA AAA AAA AAA AAA AAA        (SEQ ID NO:1)
```

FIG. 1H

SEQUENCE LISTING

<160> NUMBER OF SEQ ID NOS: 163

<210> SEQ ID NO 1
<211> LENGTH: 8091
<212> TYPE: DNA
<213> ORGANISM: Homo sapiens
<220> FEATURE:
<221> NAME/KEY: CDS
<222> LOCATION: (79)..(7041)
<223> OTHER INFORMATION: human ADNc Notch 3

<400> SEQUENCE: 1

```
acgcggcgcg gaggctggcc cgggacgcgc ccggagccca gggaaggagg gaggagggga          60
gggtcgcggc cggccgcc atg ggg ccg ggg gcc cgt ggc cgc cgc cgc cgc         111
                    Met Gly Pro Gly Ala Arg Gly Arg Arg Arg Arg
                     1               5                       10 cgt cgc ccg atg tcg ccg cca ccg cca ccg cca ccc gtg cgg gcg ctg         159
Arg Arg Pro Met Ser Pro Pro Pro Pro Pro Pro Pro Val Arg Ala Leu
             15                  20                  25 ccc ctg ctg ctg ctg cta gcg ggg ccg ggg gct gca gcc ccc cct tgc         207
Pro Leu Leu Leu Leu Leu Ala Gly Pro Gly Ala Ala Ala Pro Pro Cys
         30                  35                  40 ctg gac gga agc ccg tgt gca aat gga ggt cgt tgc acc cag ctg ccc         255
Leu Asp Gly Ser Pro Cys Ala Asn Gly Gly Arg Cys Thr Gln Leu Pro
 45                  50                  55 tcc cgg gag gct gcc tgc ctg tgc ccg cct ggc tgg gtg ggt gag cgg         303
Ser Arg Glu Ala Ala Cys Leu Cys Pro Pro Gly Trp Val Gly Glu Arg
 60                  65                  70                  75 tgt cag ctg gag gac ccc tgt cac tca ggc ccc tgt gct ggc cgt ggt         351
Cys Gln Leu Glu Asp Pro Cys His Ser Gly Pro Cys Ala Gly Arg Gly
                 80                  85                  90 gtc tgc cag agt tca gtg gtg gct ggc acc gcc cga ttc tca tgc cgg         399
Val Cys Gln Ser Ser Val Val Ala Gly Thr Ala Arg Phe Ser Cys Arg
             95                 100                 105 tgc ccc cgt ggc ttc cga ggc cct gac tgc tcc ctg cca gat ccc tgc         447
Cys Pro Arg Gly Phe Arg Gly Pro Asp Cys Ser Leu Pro Asp Pro Cys
        110                 115                 120 ctc agc agc cct tgt gcc cac ggt gcc cgc tgc tca gtg ggg ccc gat         495
Leu Ser Ser Pro Cys Ala His Gly Ala Arg Cys Ser Val Gly Pro Asp
    125                 130                 135 gga cgc ttc ctc tgc tcc tgc cca cct ggc tac cag ggc cgc agc tgc         543
Gly Arg Phe Leu Cys Ser Cys Pro Pro Gly Tyr Gln Gly Arg Ser Cys
140                 145                 150                 155 cga agc gac gtg gat gag tgc cgg gtg ggt gag ccc tgc cgc cat ggt         591
Arg Ser Asp Val Asp Glu Cys Arg Val Gly Glu Pro Cys Arg His Gly
                160                 165                 170 ggc acc tgc ctc aac aca cct ggc tcc ttc cgc tgc cag tgt cca gct         639
Gly Thr Cys Leu Asn Thr Pro Gly Ser Phe Arg Cys Gln Cys Pro Ala
            175                 180                 185 ggc tac aca ggg cca cta tgt gag aac ccc gcg gtg ccc tgt gcg ccc         687
Gly Tyr Thr Gly Pro Leu Cys Glu Asn Pro Ala Val Pro Cys Ala Pro
        190                 195                 200 tca cca tgc cgt aac ggg ggc acc tgc agg cag agt ggc gac ctc act         735
Ser Pro Cys Arg Asn Gly Gly Thr Cys Arg Gln Ser Gly Asp Leu Thr
    205                 210                 215 tac gac tgt gcc tgt ctt cct ggg ttt gag ggt cag aat tgt gaa gtg         783
Tyr Asp Cys Ala Cys Leu Pro Gly Phe Glu Gly Gln Asn Cys Glu Val
220                 225                 230                 235 aac gtg gac gac tgt cca gga cac cga tgt ctc aat ggg gga aca tgc         831
```

```
                                                              -continued

Asn Val Asp Asp Cys Pro Gly His Arg Cys Leu Asn Gly Gly Thr Cys
            240                 245                 250 gtg gat ggc gtc aac acc tat aac tgc cag tgc cct cct gag tgg aca        879
Val Asp Gly Val Asn Thr Tyr Asn Cys Gln Cys Pro Pro Glu Trp Thr
            255                 260                 265 ggc cag ttc tgc acg gag gac gtg gat gag tgt cag ctg cag ccc aac        927
Gly Gln Phe Cys Thr Glu Asp Val Asp Glu Cys Gln Leu Gln Pro Asn
            270                 275                 280 gcc tgc cac aat ggg ggt acc tgc ttc aac acg ctg ggt ggc cac agc        975
Ala Cys His Asn Gly Gly Thr Cys Phe Asn Thr Leu Gly Gly His Ser
    285                 290                 295 tgc gtg tgt gtc aat ggc tgg aca ggt gag agc tgc agt cag aat atc       1023
Cys Val Cys Val Asn Gly Trp Thr Gly Glu Ser Cys Ser Gln Asn Ile
300                 305                 310                 315 gat gac tgt gcc aca gcc gtg tgc ttc cat ggg gcc acc tgc cat gac       1071
Asp Asp Cys Ala Thr Ala Val Cys Phe His Gly Ala Thr Cys His Asp
                320                 325                 330 cgc gtg gct tct ttc tac tgt gcc tgc ccc atg ggc aag act ggc ctc       1119
Arg Val Ala Ser Phe Tyr Cys Ala Cys Pro Met Gly Lys Thr Gly Leu
            335                 340                 345 ctg tgt cac ctg gat gac gcc tgt gtc agc aac ccc tgc cac gag gat       1167
Leu Cys His Leu Asp Asp Ala Cys Val Ser Asn Pro Cys His Glu Asp
            350                 355                 360 gct atc tgt gac aca aat ccg gtg aac ggc cgg gcc att tgc acc tgt       1215
Ala Ile Cys Asp Thr Asn Pro Val Asn Gly Arg Ala Ile Cys Thr Cys
365                 370                 375 cct ccc ggc ttc acg ggt ggg gca tgt gac cag gat gtg gac gag tgc       1263
Pro Pro Gly Phe Thr Gly Gly Ala Cys Asp Gln Asp Val Asp Glu Cys
380                 385                 390                 395 tct atc ggc gcc aac ccc tgc gag cac ttg ggc agg tgc gtg aac acg       1311
Ser Ile Gly Ala Asn Pro Cys Glu His Leu Gly Arg Cys Val Asn Thr
                400                 405                 410 cag ggc tcc ttc ctg tgc cag tgc ggt cgt ggc tac act gga cct cgc       1359
Gln Gly Ser Phe Leu Cys Gln Cys Gly Arg Gly Tyr Thr Gly Pro Arg
            415                 420                 425 tgt gag acc gat gtc aac gag tgt ctg tcg ggg ccc tgc cga aac cag       1407
Cys Glu Thr Asp Val Asn Glu Cys Leu Ser Gly Pro Cys Arg Asn Gln
            430                 435                 440 gcc acg tgc ctc gac cgc ata ggc cag ttc acc tgt atc tgt atg gca       1455
Ala Thr Cys Leu Asp Arg Ile Gly Gln Phe Thr Cys Ile Cys Met Ala
    445                 450                 455 ggc ttc aca gga acc tat tgc gag gtg gac att gac gag tgt cag agt       1503
Gly Phe Thr Gly Thr Tyr Cys Glu Val Asp Ile Asp Glu Cys Gln Ser
460                 465                 470                 475 agc ccc tgt gtc aac ggt ggg gtc tgc aag gac cga gtc aat ggc ttc       1551
Ser Pro Cys Val Asn Gly Gly Val Cys Lys Asp Arg Val Asn Gly Phe
                480                 485                 490 agc tgc acc tgc ccc tcg ggc ttc agc ggc tcc acg tgt cag ctg gac       1599
Ser Cys Thr Cys Pro Ser Gly Phe Ser Gly Ser Thr Cys Gln Leu Asp
            495                 500                 505 gtg gac gaa tgc gcc agc acg ccc tgc agg aat ggc gcc aaa tgc gtg       1647
Val Asp Glu Cys Ala Ser Thr Pro Cys Arg Asn Gly Ala Lys Cys Val
            510                 515                 520 gac cag ccc gat ggc tac gag tgc cgc tgt gcc gag ggc ttt gag ggc       1695
Asp Gln Pro Asp Gly Tyr Glu Cys Arg Cys Ala Glu Gly Phe Glu Gly
    525                 530                 535 acg ctg tgt gat cgc aac gtg gac gac tgc tcc cct gac cca tgc cac       1743
Thr Leu Cys Asp Arg Asn Val Asp Asp Cys Ser Pro Asp Pro Cys His
540                 545                 550                 555
```

```
cat ggt cgc tgc gtg gat ggc atc gcc agc ttc tca tgt gcc tgt gct    1791
His Gly Arg Cys Val Asp Gly Ile Ala Ser Phe Ser Cys Ala Cys Ala
                560                 565                 570 cct ggc tac acg ggc aca cgc tgc gag agc cag gtg gac gaa tgc cgc    1839
Pro Gly Tyr Thr Gly Thr Arg Cys Glu Ser Gln Val Asp Glu Cys Arg
            575                 580                 585 agc cag ccc tgc cgc cat ggc ggc aaa tgc cta gac ctg gtg gac aag    1887
Ser Gln Pro Cys Arg His Gly Gly Lys Cys Leu Asp Leu Val Asp Lys
        590                 595                 600 tac ctc tgc cgc tgc cct tct ggg acc aca ggt gtg aac tgc gaa gtg    1935
Tyr Leu Cys Arg Cys Pro Ser Gly Thr Thr Gly Val Asn Cys Glu Val
    605                 610                 615 aac att gac gac tgt gcc agc aac ccc tgc acc ttt gga gtc tgc cgt    1983
Asn Ile Asp Asp Cys Ala Ser Asn Pro Cys Thr Phe Gly Val Cys Arg
620                 625                 630                 635 gat ggc atc aac cgc tac gac tgt gtc tgc caa cct ggc ttc aca ggg    2031
Asp Gly Ile Asn Arg Tyr Asp Cys Val Cys Gln Pro Gly Phe Thr Gly
                640                 645                 650 ccc ctt tgt aac gtg gag atc aat gag tgt gct tcc agc cca tgc ggc    2079
Pro Leu Cys Asn Val Glu Ile Asn Glu Cys Ala Ser Ser Pro Cys Gly
            655                 660                 665 gag gga ggt tcc tgt gtg gat ggg gaa aat ggc ttc cgc tgc ctc tgc    2127
Glu Gly Gly Ser Cys Val Asp Gly Glu Asn Gly Phe Arg Cys Leu Cys
        670                 675                 680 ccg cct ggc tcc ttg ccc cca ctc tgc ctc ccc cgc agc cat ccc tgt    2175
Pro Pro Gly Ser Leu Pro Pro Leu Cys Leu Pro Pro Ser His Pro Cys
    685                 690                 695 gcc cat gag ccc tgc agt cac ggc atc tgc tat gat gca cct ggc ggg    2223
Ala His Glu Pro Cys Ser His Gly Ile Cys Tyr Asp Ala Pro Gly Gly
700                 705                 710                 715 ttc cgc tgt gtg tgt gag cct ggc tgg agt ggc ccc cgc tgc agc cag    2271
Phe Arg Cys Val Cys Glu Pro Gly Trp Ser Gly Pro Arg Cys Ser Gln
                720                 725                 730 agc ctg gcc cga gac gcc tgt gag tcc cag ccg tgc agg gcc ggt ggg    2319
Ser Leu Ala Arg Asp Ala Cys Glu Ser Gln Pro Cys Arg Ala Gly Gly
            735                 740                 745 aca tgc agc agc gat gga atg ggt ttc cac tgc acc tgc ccg cct ggt    2367
Thr Cys Ser Ser Asp Gly Met Gly Phe His Cys Thr Cys Pro Pro Gly
        750                 755                 760 gtc cag gga cgt cag tgt gaa ctc ctc tcc ccc tgc acc ccg aac ccc    2415
Val Gln Gly Arg Gln Cys Glu Leu Leu Ser Pro Cys Thr Pro Asn Pro
    765                 770                 775 tgt gag cat ggg ggc cgc tgc gag tct gcc cct ggc cag ctg cct gtc    2463
Cys Glu His Gly Gly Arg Cys Glu Ser Ala Pro Gly Gln Leu Pro Val
780                 785                 790                 795 tgc tcc tgc ccc cag ggc tgg caa ggc cca cga tgc cag cag gat gtg    2511
Cys Ser Cys Pro Gln Gly Trp Gln Gly Pro Arg Cys Gln Gln Asp Val
                800                 805                 810 gac gag tgt gct ggc ccc gca ccc tgt ggc cct cat ggt atc tgc acc    2559
Asp Glu Cys Ala Gly Pro Ala Pro Cys Gly Pro His Gly Ile Cys Thr
            815                 820                 825 aac ctg gca ggg agt ttc agc tgc acc tgc cat gga ggg tac act ggc    2607
Asn Leu Ala Gly Ser Phe Ser Cys Thr Cys His Gly Gly Tyr Thr Gly
        830                 835                 840 cct tcc tgt gat cag gac atc aat gac tgt gac ccc aac cca tgc ctg    2655
Pro Ser Cys Asp Gln Asp Ile Asn Asp Cys Asp Pro Asn Pro Cys Leu
    845                 850                 855 aac ggt ggc tcg tgc caa gac ggc gtg ggc tcc ttt tcc tgc tcc tgc    2703
Asn Gly Gly Ser Cys Gln Asp Gly Val Gly Ser Phe Ser Cys Ser Cys
860                 865                 870                 875
```

-continued

```
ctc cct ggt ttc gcc ggc cca cga tgc gcc cgc gat gtg gat gag tgc      2751
Leu Pro Gly Phe Ala Gly Pro Arg Cys Ala Arg Asp Val Asp Glu Cys
            880                 885                 890 ctg agc aac ccc tgc ggc ccg ggc acc tgt acc gac cac gtg gcc tcc      2799
Leu Ser Asn Pro Cys Gly Pro Gly Thr Cys Thr Asp His Val Ala Ser
            895                 900                 905 ttc acc tgc acc tgc ccg ccg ggc tac gga ggc ttc cac tgc gaa cag      2847
Phe Thr Cys Thr Cys Pro Pro Gly Tyr Gly Gly Phe His Cys Glu Gln
            910                 915                 920 gac ctg ccc gac tgc agc ccc agc tcc tgc ttc aat ggc ggg acc tgt      2895
Asp Leu Pro Asp Cys Ser Pro Ser Ser Cys Phe Asn Gly Gly Thr Cys
        925                 930                 935 gtg gac ggc gtg aac tcg ttc agc tgc ctg tgc cgt ccc ggc tac aca      2943
Val Asp Gly Val Asn Ser Phe Ser Cys Leu Cys Arg Pro Gly Tyr Thr
    940                 945                 950                 955 gga gcc cac tgc caa cat gag gca gac ccc tgc ctc tcg cgg ccc tgc      2991
Gly Ala His Cys Gln His Glu Ala Asp Pro Cys Leu Ser Arg Pro Cys
                960                 965                 970 cta cac ggg ggc gtc tgc agc gcc gcc cac cct ggc ttc cgc tgc acc      3039
Leu His Gly Gly Val Cys Ser Ala Ala His Pro Gly Phe Arg Cys Thr
        975                 980                 985 tgc ctc gag agc ttc acg ggc ccg cag tgc cag acg ctg gtg gat tgg      3087
Cys Leu Glu Ser Phe Thr Gly Pro Gln Cys Gln Thr Leu Val Asp Trp
    990                 995                 1000 tgc agc cgc cag cct tgt caa aac ggg ggt cgc tgc gtc cag act ggg      3135
Cys Ser Arg Gln Pro Cys Gln Asn Gly Gly Arg Cys Val Gln Thr Gly
    1005                1010                1015 gcc tat tgc ctt tgt ccc cct gga tgg agc gga cgc ctc tgt gac atc      3183
Ala Tyr Cys Leu Cys Pro Pro Gly Trp Ser Gly Arg Leu Cys Asp Ile
1020                1025                1030                1035 cga agc ttg ccc tgc agg gag gcc gca gcc cag atc ggg gtg cgg ctg      3231
Arg Ser Leu Pro Cys Arg Glu Ala Ala Ala Gln Ile Gly Val Arg Leu
            1040                1045                1050 gag cag ctg tgt cag gcg ggt ggg cag tgt gtg gat gaa gac agc tcc      3279
Glu Gln Leu Cys Gln Ala Gly Gly Gln Cys Val Asp Glu Asp Ser Ser
        1055                1060                1065 cac tac tgc gtg tgc cca gag ggc cgt act ggt agc cac tgt gag cag      3327
His Tyr Cys Val Cys Pro Glu Gly Arg Thr Gly Ser His Cys Glu Gln
    1070                1075                1080 gag gtg gac ccc tgc ttg gcc cag ccc tgc cag cat ggg ggg acc tgc      3375
Glu Val Asp Pro Cys Leu Ala Gln Pro Cys Gln His Gly Gly Thr Cys
1085                1090                1095 cgt ggc tat atg ggg ggc tac atg tgt gag tgt ctt cct ggc tac aat      3423
Arg Gly Tyr Met Gly Gly Tyr Met Cys Glu Cys Leu Pro Gly Tyr Asn
1100                1105                1110                1115 ggt gat aac tgt gag gac gac gtg gac gag tgt gcc tcc cag ccc tgc      3471
Gly Asp Asn Cys Glu Asp Asp Val Asp Glu Cys Ala Ser Gln Pro Cys
        1120                1125                1130 cag cac ggg ggt tca tgc att gac ctc gtg gcc cgc tat ctc tgc tcc      3519
Gln His Gly Gly Ser Cys Ile Asp Leu Val Ala Arg Tyr Leu Cys Ser
        1135                1140                1145 tgt ccc cca gga acg ctg ggg gtg ctc tgc gag att aat gag gat gac      3567
Cys Pro Pro Gly Thr Leu Gly Val Leu Cys Glu Ile Asn Glu Asp Asp
    1150                1155                1160 tgc ggc cca ggc cca ccg ctg gac tca ggg ccc cgg tgc cta cac aat      3615
Cys Gly Pro Gly Pro Pro Leu Asp Ser Gly Pro Arg Cys Leu His Asn
    1165                1170                1175 ggc acc tgc gtg gac ctg gtg ggt ggt ttc cgc tgc acc tgt ccc cca      3663
Gly Thr Cys Val Asp Leu Val Gly Gly Phe Arg Cys Thr Cys Pro Pro
```

-continued

| | |
|---|---|
| 1180 1185 1190 1195 | |
| gga tac act ggt ttg cgc tgc gag gca gac atc aat gag tgt cgc tca<br>Gly Tyr Thr Gly Leu Arg Cys Glu Ala Asp Ile Asn Glu Cys Arg Ser<br>                  1200                    1205                    1210 | 3711 |
| ggt gcc tgc cac gcg gca cac acc cgg gac tgc ctg cag gac cca ggc<br>Gly Ala Cys His Ala Ala His Thr Arg Asp Cys Leu Gln Asp Pro Gly<br>1215                    1220                    1225 | 3759 |
| gga ggt ttc cgt tgc ctt tgt cat gct ggc ttc tca ggt cct cgc tgt<br>Gly Gly Phe Arg Cys Leu Cys His Ala Gly Phe Ser Gly Pro Arg Cys<br>        1230                    1235                    1240 | 3807 |
| cag act gtc ctg tct ccc tgc gag tcc cag cca tgc cag cat gga ggc<br>Gln Thr Val Leu Ser Pro Cys Glu Ser Gln Pro Cys Gln His Gly Gly<br>   1245                    1250                    1255 | 3855 |
| cag tgc cgt cct agc ccg ggt cct ggg ggt ggg ctg acc ttc acc tgt<br>Gln Cys Arg Pro Ser Pro Gly Pro Gly Gly Gly Leu Thr Phe Thr Cys<br>1260                    1265                    1270                    1275 | 3903 |
| cac tgt gcc cag ccg ttc tgg ggt ccg cgt tgc gag cgg gtg gcg cgc<br>His Cys Ala Gln Pro Phe Trp Gly Pro Arg Cys Glu Arg Val Ala Arg<br>                  1280                    1285                    1290 | 3951 |
| tcc tgc cgg gag ctg cag tgc ccg gtg ggc gtc cca tgc cag cag acg<br>Ser Cys Arg Glu Leu Gln Cys Pro Val Gly Val Pro Cys Gln Gln Thr<br>1295                    1300                    1305 | 3999 |
| ccc cgc ggg ccg cgc tgc gcc tgc ccc cca ggg ttg tcg gga ccc tcc<br>Pro Arg Gly Pro Arg Cys Ala Cys Pro Pro Gly Leu Ser Gly Pro Ser<br>        1310                    1315                    1320 | 4047 |
| tgc cgc agc ttc ccg ggg tcg ccg ccg ggg gcc agc aac gcc agc tgc<br>Cys Arg Ser Phe Pro Gly Ser Pro Pro Gly Ala Ser Asn Ala Ser Cys<br>   1325                    1330                    1335 | 4095 |
| gcg gcc gcc ccc tgt ctc cac ggg ggc tcc tgc cgc ccc gcg ccg ctc<br>Ala Ala Ala Pro Cys Leu His Gly Gly Ser Cys Arg Pro Ala Pro Leu<br>1340                    1345                    1350                    1355 | 4143 |
| gcg ccc ttc ttc cgc tgc gct tgc gcg cag ggc tgg acc ggg ccg cgc<br>Ala Pro Phe Phe Arg Cys Ala Cys Ala Gln Gly Trp Thr Gly Pro Arg<br>                  1360                    1365                    1370 | 4191 |
| tgc gag gcg ccc gcc gcg gca ccc gag gtc tcg gag gag ccg cgg tgc<br>Cys Glu Ala Pro Ala Ala Ala Pro Glu Val Ser Glu Glu Pro Arg Cys<br>1375                    1380                    1385 | 4239 |
| ccg cgc gcc gcc tgc cag gcc aag cgc ggg gac cag cgc tgc gac cgc<br>Pro Arg Ala Ala Cys Gln Ala Lys Arg Gly Asp Gln Arg Cys Asp Arg<br>        1390                    1395                    1400 | 4287 |
| gag tgc aac agc cca ggc tgc ggc tgg gac ggc ggc gac tgc tcg ctg<br>Glu Cys Asn Ser Pro Gly Cys Gly Trp Asp Gly Gly Asp Cys Ser Leu<br>1405                    1410                    1415 | 4335 |
| agc gtg ggc gac ccc tgg cgg caa tgc gag gcg ctg cag tgc tgg cgc<br>Ser Val Gly Asp Pro Trp Arg Gln Cys Glu Ala Leu Gln Cys Trp Arg<br>1420                    1425                    1430                    1435 | 4383 |
| ctc ttc aac aac agc cgc tgc gac ccc gcc tgc agc tcg ccc gcc tgc<br>Leu Phe Asn Asn Ser Arg Cys Asp Pro Ala Cys Ser Ser Pro Ala Cys<br>                  1440                    1445                    1450 | 4431 |
| ctc tac gac aac ttc gac tgc cac gcc ggt ggc cgc gag cgc act tgc<br>Leu Tyr Asp Asn Phe Asp Cys His Ala Gly Gly Arg Glu Arg Thr Cys<br>1455                    1460                    1465 | 4479 |
| aac ccg gtg tac gag aag tac tgc gcc gac cac ttt gcc gac ggc cgc<br>Asn Pro Val Tyr Glu Lys Tyr Cys Ala Asp His Phe Ala Asp Gly Arg<br>        1470                    1475                    1480 | 4527 |
| tgc gac cag ggc tgc aac acg gag gag tgc ggc tgg gat ggg ctg gat<br>Cys Asp Gln Gly Cys Asn Thr Glu Glu Cys Gly Trp Asp Gly Leu Asp<br>   1485                    1490                    1495 | 4575 |
| tgt gcc agc gag gtg ccg gcc ctg ctg gcc cgc ggc gtg ctg gtg ctc | 4623 |

```
                                                        -continued

Cys Ala Ser Glu Val Pro Ala Leu Leu Ala Arg Gly Val Leu Val Leu
1500                1505                1510                1515 aca gtg ctg ctg ccg ccg gag gag cta ctg cgt tcc agc gcc gac ttt       4671
Thr Val Leu Leu Pro Pro Glu Glu Leu Leu Arg Ser Ser Ala Asp Phe
            1520                1525                1530 ctg cag cgg ctc agc gcc atc ctg cgc acc tcg ctg cgc ttc cgc ctg       4719
Leu Gln Arg Leu Ser Ala Ile Leu Arg Thr Ser Leu Arg Phe Arg Leu
        1535                1540                1545 gac gcg cac ggc cag gcc atg gtc ttc cct tac cac cgg cct agt cct       4767
Asp Ala His Gly Gln Ala Met Val Phe Pro Tyr His Arg Pro Ser Pro
    1550                1555                1560 ggc tcc gaa ccc cgg gcc cgt cgg gag ctg gcc ccc gag gtg atc ggc       4815
Gly Ser Glu Pro Arg Ala Arg Arg Glu Leu Ala Pro Glu Val Ile Gly
1565                1570                1575 tcg gta gta atg ctg gag att gac aac cgg ctc tgc ctg cag tcg cct       4863
Ser Val Val Met Leu Glu Ile Asp Asn Arg Leu Cys Leu Gln Ser Pro
1580                1585                1590                1595 gag aat gat cac tgc ttc ccc gat gcc cag agc gcc gct gac tac ctg       4911
Glu Asn Asp His Cys Phe Pro Asp Ala Gln Ser Ala Ala Asp Tyr Leu
            1600                1605                1610 gga gcg ttg tca gcg gtg gag cgc ctg gac ttc ccg tac cca ctg cgg       4959
Gly Ala Leu Ser Ala Val Glu Arg Leu Asp Phe Pro Tyr Pro Leu Arg
        1615                1620                1625 gac gtg cgg ggg gag ccg ctg gag cct cca gaa ccc agc gtc ccg ctg       5007
Asp Val Arg Gly Glu Pro Leu Glu Pro Pro Glu Pro Ser Val Pro Leu
    1630                1635                1640 ctg cca ctg cta gtg gcg ggc gct gtc ttg ctg ctg gtc att ctc gtc       5055
Leu Pro Leu Leu Val Ala Gly Ala Val Leu Leu Leu Val Ile Leu Val
1645                1650                1655 ctg ggt gtc atg gtg gcc cgg cgc aag cgc gag cac agc acc ctc tgg       5103
Leu Gly Val Met Val Ala Arg Arg Lys Arg Glu His Ser Thr Leu Trp
1660                1665                1670                1675 ttc cct gag ggc ttc tca ctg cac aag gac gtg gcc tct ggt cac aag       5151
Phe Pro Glu Gly Phe Ser Leu His Lys Asp Val Ala Ser Gly His Lys
            1680                1685                1690 ggc cgg cgg gaa ccc gtg ggc cag gac gcg ctg ggc atg aag aac atg       5199
Gly Arg Arg Glu Pro Val Gly Gln Asp Ala Leu Gly Met Lys Asn Met
        1695                1700                1705 gcc aag ggt gag agc ctg atg ggg gag gtg gcc aca gac tgg atg gac       5247
Ala Lys Gly Glu Ser Leu Met Gly Glu Val Ala Thr Asp Trp Met Asp
    1710                1715                1720 aca gag tgc cca gag gcc aag cgg cta aag gta gag gag cca ggc atg       5295
Thr Glu Cys Pro Glu Ala Lys Arg Leu Lys Val Glu Glu Pro Gly Met
1725                1730                1735 ggg gct gag gag gct gtg gat tgc cgt cag tgg act caa cac cat ctg       5343
Gly Ala Glu Glu Ala Val Asp Cys Arg Gln Trp Thr Gln His His Leu
1740                1745                1750                1755 gtt gct gct gac atc cgc gtg gca cca gcc atg gca ctg aca cca cca       5391
Val Ala Ala Asp Ile Arg Val Ala Pro Ala Met Ala Leu Thr Pro Pro
            1760                1765                1770 cag ggc gac gca gat gct gat ggc atg gat gtc aat gtg cgt ggc cca       5439
Gln Gly Asp Ala Asp Ala Asp Gly Met Asp Val Asn Val Arg Gly Pro
        1775                1780                1785 gat ggc ttc acc ccg cta atg ctg gct tcc ttc tgt ggg ggg gct ctg       5487
Asp Gly Phe Thr Pro Leu Met Leu Ala Ser Phe Cys Gly Gly Ala Leu
    1790                1795                1800 gag cca atg cca act gaa gag gat gag gca gat gac aca tca gct agc       5535
Glu Pro Met Pro Thr Glu Glu Asp Glu Ala Asp Asp Thr Ser Ala Ser
1805                1810                1815
```

-continued

```
atc atc tcc gac ctg atc tgc cag ggg gct cag ctt ggg gca cgg act          5583
Ile Ile Ser Asp Leu Ile Cys Gln Gly Ala Gln Leu Gly Ala Arg Thr
1820            1825                1830                1835 gac cgt act ggc gag act gct ttg cac ctg gct gcc cgt tat gcc cgt          5631
Asp Arg Thr Gly Glu Thr Ala Leu His Leu Ala Ala Arg Tyr Ala Arg
            1840                1845                1850 gct gat gca gcc aag cgg ctg ctg gat gct ggg gca gac acc aat gcc          5679
Ala Asp Ala Ala Lys Arg Leu Leu Asp Ala Gly Ala Asp Thr Asn Ala
1855                1860                1865 cag gac cac tca ggc cgc act ccc ctg cac aca gct gtc aca gcc gat          5727
Gln Asp His Ser Gly Arg Thr Pro Leu His Thr Ala Val Thr Ala Asp
    1870                1875                1880 gcc cag ggt gtc ttc cag att ctc atc cga aac cgc tct aca gac ttg          5775
Ala Gln Gly Val Phe Gln Ile Leu Ile Arg Asn Arg Ser Thr Asp Leu
        1885                1890                1895 gat gcc cgc atg gca gat ggc tca acg gca ctg atc ctg gcg gcc cgc          5823
Asp Ala Arg Met Ala Asp Gly Ser Thr Ala Leu Ile Leu Ala Ala Arg
1900                1905                1910                1915 ctg gca gta gag ggc atg gtg gaa gag ctc atc gcc agc cat gct gat          5871
Leu Ala Val Glu Gly Met Val Glu Glu Leu Ile Ala Ser His Ala Asp
            1920                1925                1930 gtc aat gct gtg gat gag ctt ggg aaa tca gcc tta cac tgg gct gcg          5919
Val Asn Ala Val Asp Glu Leu Gly Lys Ser Ala Leu His Trp Ala Ala
1935                1940                1945 gct gtg aac aac gtg gaa gcc act ttg gcc ctg ctc aaa aat gga gcc          5967
Ala Val Asn Asn Val Glu Ala Thr Leu Ala Leu Leu Lys Asn Gly Ala
    1950                1955                1960 aat aag gac atg cag gat agc aag gag gag acc ccc cta ttc ctg gcc          6015
Asn Lys Asp Met Gln Asp Ser Lys Glu Glu Thr Pro Leu Phe Leu Ala
1965                1970                1975 gcc cgc gag ggc agc tat gag gct gcc aag ctg ctg ttg gac cac ttt          6063
Ala Arg Glu Gly Ser Tyr Glu Ala Ala Lys Leu Leu Leu Asp His Phe
1980                1985                1990                1995 gcc aac cgt gag atc acc gac cac ctg gac agg ctg ccg cgg gac gta          6111
Ala Asn Arg Glu Ile Thr Asp His Leu Asp Arg Leu Pro Arg Asp Val
            2000                2005                2010 gcc cag gag aga ctg cac cag gac atc gtg cgc ttg ctg gat caa ccc          6159
Ala Gln Glu Arg Leu His Gln Asp Ile Val Arg Leu Leu Asp Gln Pro
2015                2020                2025 agt ggg ccc cgc agc ccc ccc ggt ccc cac ggc ctg ggg cct ctg ctc          6207
Ser Gly Pro Arg Ser Pro Pro Gly Pro His Gly Leu Gly Pro Leu Leu
            2030                2035                2040 tgt cct cca ggg gcc ttc ctc cct ggc ctc aaa gcg gca cag tcg ggg          6255
Cys Pro Pro Gly Ala Phe Leu Pro Gly Leu Lys Ala Ala Gln Ser Gly
2045                2050                2055 tcc aag aag agc agg agg ccc ccc ggg aag gcg ggg ctg ggg ccg cag          6303
Ser Lys Lys Ser Arg Arg Pro Pro Gly Lys Ala Gly Leu Gly Pro Gln
2060                2065                2070                2075 ggg ccc cgg ggg cgg ggc aag aag ctg acg ctg gcc tgc ccg ggc ccc          6351
Gly Pro Arg Gly Arg Gly Lys Lys Leu Thr Leu Ala Cys Pro Gly Pro
            2080                2085                2090 ctg gct gac agc tcg gtc acg ctg tcg ccc gtg gac tcg ctg gac tcc          6399
Leu Ala Asp Ser Ser Val Thr Leu Ser Pro Val Asp Ser Leu Asp Ser
2095                2100                2105 ccg cgg cct ttc ggt ggg ccc cct gct tcc cct ggt ggc ttc ccc ctt          6447
Pro Arg Pro Phe Gly Gly Pro Pro Ala Ser Pro Gly Gly Phe Pro Leu
            2110                2115                2120 gag ggg ccc tat gca gct gcc act gcc act gca gtg tct ctg gca cag          6495
Glu Gly Pro Tyr Ala Ala Ala Thr Ala Thr Ala Val Ser Leu Ala Gln
2125                2130                2135
```

```
ctt ggt ggc cca ggc cgg gca ggt cta ggg cgc cag ccc cct gga gga    6543
Leu Gly Gly Pro Gly Arg Ala Gly Leu Gly Arg Gln Pro Pro Gly Gly
2140            2145                2150                2155 tgt gta ctc agc ctg ggc ctg ctg aac cct gtg gct gtg ccc ctc gat    6591
Cys Val Leu Ser Leu Gly Leu Leu Asn Pro Val Ala Val Pro Leu Asp
        2160                2165                2170 tgg gcc cgg ctg ccc cca cct gcc cct cca ggc ccc tcg ttc ctg ctg    6639
Trp Ala Arg Leu Pro Pro Pro Ala Pro Pro Gly Pro Ser Phe Leu Leu
            2175                2180                2185 cca ctg gcg ccg gga ccc cag ctg ctc aac cca ggg acc ccc gtc tcc    6687
Pro Leu Ala Pro Gly Pro Gln Leu Leu Asn Pro Gly Thr Pro Val Ser
    2190                2195                2200 ccg cag gag cgg ccc ccg cct tac ctg gca gtc cca gga cat ggc gag    6735
Pro Gln Glu Arg Pro Pro Pro Tyr Leu Ala Val Pro Gly His Gly Glu
2205                2210                2215 gag tac ccg gtg gct ggg gca cac agc agc ccc cca aag gcc cgc ttc    6783
Glu Tyr Pro Val Ala Gly Ala His Ser Ser Pro Pro Lys Ala Arg Phe
2220                2225                2230                2235 ctg cgg gtt ccc agt gag cac cct tac ctg acc cca tcc ccc gaa tcc    6831
Leu Arg Val Pro Ser Glu His Pro Tyr Leu Thr Pro Ser Pro Glu Ser
            2240                2245                2250 cct gag cac tgg gcc agc ccc tca cct ccc tcc ctc tca gac tgg tcc    6879
Pro Glu His Trp Ala Ser Pro Ser Pro Pro Ser Leu Ser Asp Trp Ser
                2255                2260                2265 gaa tcc acg cct agc cca gcc act gcc act ggg gcc atg gcc acc acc    6927
Glu Ser Thr Pro Ser Pro Ala Thr Ala Thr Gly Ala Met Ala Thr Thr
            2270                2275                2280 act ggg gca ctg cct gcc cag cca ctt ccc ttg tct gtt ccc agc tcc    6975
Thr Gly Ala Leu Pro Ala Gln Pro Leu Pro Leu Ser Val Pro Ser Ser
    2285                2290                2295 ctt gct cag gcc cag acc cag ctg ggg ccc cag ccg gaa gtt acc ccc    7023
Leu Ala Gln Ala Gln Thr Gln Leu Gly Pro Gln Pro Glu Val Thr Pro
2300                2305                2310                2315 aag agg caa gtg ttg gcc tgagacgctc gtcagttctt agatcttggg           7071
Lys Arg Gln Val Leu Ala
                2320 ggcctaaaga gaccccgtc ctgcctcctt tctttctctg tctcttcctt ccttttagtc   7131 tttttcatcc tcttctcttt ccaccaaccc tcctgcatcc ttgccttgca gcgtgaccga  7191 gataggtcat cagcccaggg cttcagtctt cctttattta taatgggtgg gggctaccac  7251 ccaccctctc agtcttgtga agagtctggg acctccttct tccccacttc tctcttccct  7311 cattcctttc tctctccttc tggcctctca tttccttaca ctctgacatg aatgaattat  7371 tattattttt cttttctttt tttttttac attttgtata gaaacaaatt catttaaaca   7431 aacttattat tattatttttt tacaaaatat atatatggag atgctccctc ccctgtgaa  7491 ccccccagtg ccccgtggg gctgagtctg tgggcccatt cggccaagct ggattctgtg   7551 tacctagtac acaggcatga ctgggatccc gtgtaccgag tacacgaccc aggtatgtac  7611 caagtaggca cccttgggcg cacccactgg ggccaggggt cggggagtg ttgggagcct   7671 cctcccacc ccacctccct cacttcactg cattccagat tggacatgtt ccatagcctt   7731 gctggggaag ggcccactgc caactccctc tgccccagcc ccaccttgg ccatctccct   7791 ttgggaacta gggggctgct ggtgggaaat gggagccagg gcagatgtat gcattccttt  7851 atgtccctgt aaatgtggga ctacaagaag aggagctgcc tgagtggtac tttctcttcc  7911 tggtaatcct ctgcccagc cttatggcag aatagaggta tttttaggct attttgtaa   7971
```

-continued

```
tatggcttct ggtcaaaatc cctgtgtagc tgaattccca agccctgcat tgtacagccc    8031
cccactcccc tcaccaccta ataaaggaat agttaacact caaaaaaaaa aaaaaaaaa     8091
```

<210> SEQ ID NO 2
<211> LENGTH: 2321
<212> TYPE: PRT
<213> ORGANISM: Homo sapiens
<220> FEATURE:
<223> OTHER INFORMATION: human ADNc Notch 3

<400> SEQUENCE: 2

```
Met Gly Pro Gly Ala Arg Gly Arg Arg Arg Arg Pro Met Ser
 1               5                  10                  15

Pro Pro Pro Pro Pro Pro Val Arg Ala Leu Pro Leu Leu Leu Leu
            20                  25                  30

Leu Ala Gly Pro Gly Ala Ala Ala Pro Pro Cys Leu Asp Gly Ser Pro
        35                  40                  45

Cys Ala Asn Gly Gly Arg Cys Thr Gln Leu Pro Ser Arg Glu Ala Ala
    50                  55                  60

Cys Leu Cys Pro Pro Gly Trp Val Gly Glu Arg Cys Gln Leu Glu Asp
65                  70                  75                  80

Pro Cys His Ser Gly Pro Cys Ala Gly Arg Gly Val Cys Gln Ser Ser
                85                  90                  95

Val Val Ala Gly Thr Ala Arg Phe Ser Cys Arg Cys Pro Arg Gly Phe
           100                 105                 110

Arg Gly Pro Asp Cys Ser Leu Pro Asp Pro Cys Leu Ser Ser Pro Cys
       115                 120                 125

Ala His Gly Ala Arg Cys Ser Val Gly Pro Asp Gly Arg Phe Leu Cys
   130                 135                 140

Ser Cys Pro Pro Gly Tyr Gln Gly Arg Ser Cys Arg Ser Asp Val Asp
145                 150                 155                 160

Glu Cys Arg Val Gly Glu Pro Cys Arg His Gly Gly Thr Cys Leu Asn
               165                 170                 175

Thr Pro Gly Ser Phe Arg Cys Gln Cys Pro Ala Gly Tyr Thr Gly Pro
           180                 185                 190

Leu Cys Glu Asn Pro Ala Val Pro Cys Ala Pro Ser Pro Cys Arg Asn
       195                 200                 205

Gly Gly Thr Cys Arg Gln Ser Gly Asp Leu Thr Tyr Asp Cys Ala Cys
   210                 215                 220

Leu Pro Gly Phe Glu Gly Gln Asn Cys Glu Val Asn Val Asp Asp Cys
225                 230                 235                 240

Pro Gly His Arg Cys Leu Asn Gly Gly Thr Cys Val Asp Gly Val Asn
               245                 250                 255

Thr Tyr Asn Cys Gln Cys Pro Pro Glu Trp Thr Gly Gln Phe Cys Thr
           260                 265                 270

Glu Asp Val Asp Glu Cys Gln Leu Gln Pro Asn Ala Cys His Asn Gly
       275                 280                 285

Gly Thr Cys Phe Asn Thr Leu Gly Gly His Ser Cys Val Cys Val Asn
   290                 295                 300

Gly Trp Thr Gly Glu Ser Cys Ser Gln Asn Ile Asp Asp Cys Ala Thr
305                 310                 315                 320

Ala Val Cys Phe His Gly Ala Thr Cys His Asp Arg Val Ala Ser Phe
               325                 330                 335

Tyr Cys Ala Cys Pro Met Gly Lys Thr Gly Leu Leu Cys His Leu Asp
           340                 345                 350
```

```
Asp Ala Cys Val Ser Asn Pro Cys His Glu Asp Ala Ile Cys Asp Thr
        355                 360                 365
Asn Pro Val Asn Gly Arg Ala Ile Cys Thr Cys Pro Pro Gly Phe Thr
    370                 375                 380
Gly Gly Ala Cys Asp Gln Asp Val Asp Glu Cys Ser Ile Gly Ala Asn
385                 390                 395                 400
Pro Cys Glu His Leu Gly Arg Cys Val Asn Thr Gln Gly Ser Phe Leu
                405                 410                 415
Cys Gln Cys Gly Arg Gly Tyr Thr Gly Pro Arg Cys Glu Thr Asp Val
            420                 425                 430
Asn Glu Cys Leu Ser Gly Pro Cys Arg Asn Gln Ala Thr Cys Leu Asp
            435                 440                 445
Arg Ile Gly Gln Phe Thr Cys Ile Cys Met Ala Gly Phe Thr Gly Thr
    450                 455                 460
Tyr Cys Glu Val Asp Ile Asp Glu Cys Gln Ser Ser Pro Cys Val Asn
465                 470                 475                 480
Gly Gly Val Cys Lys Asp Arg Val Asn Gly Phe Ser Cys Thr Cys Pro
            485                 490                 495
Ser Gly Phe Ser Gly Ser Thr Cys Gln Leu Asp Val Asp Glu Cys Ala
            500                 505                 510
Ser Thr Pro Cys Arg Asn Gly Ala Lys Cys Val Asp Gln Pro Asp Gly
        515                 520                 525
Tyr Glu Cys Arg Cys Ala Glu Gly Phe Glu Gly Thr Leu Cys Asp Arg
        530                 535                 540
Asn Val Asp Asp Cys Ser Pro Asp Pro Cys His His Gly Arg Cys Val
545                 550                 555                 560
Asp Gly Ile Ala Ser Phe Ser Cys Ala Cys Ala Pro Gly Tyr Thr Gly
                565                 570                 575
Thr Arg Cys Glu Ser Gln Val Asp Glu Cys Arg Ser Gln Pro Cys Arg
            580                 585                 590
His Gly Gly Lys Cys Leu Asp Leu Val Asp Lys Tyr Leu Cys Arg Cys
        595                 600                 605
Pro Ser Gly Thr Thr Gly Val Asn Cys Glu Val Asn Ile Asp Asp Cys
    610                 615                 620
Ala Ser Asn Pro Cys Thr Phe Gly Val Cys Arg Asp Gly Ile Asn Arg
625                 630                 635                 640
Tyr Asp Cys Val Cys Gln Pro Gly Phe Thr Gly Pro Leu Cys Asn Val
                645                 650                 655
Glu Ile Asn Glu Cys Ala Ser Ser Pro Cys Gly Glu Gly Gly Ser Cys
            660                 665                 670
Val Asp Gly Glu Asn Gly Phe Arg Cys Leu Cys Pro Pro Gly Ser Leu
        675                 680                 685
Pro Pro Leu Cys Leu Pro Pro Ser His Pro Cys Ala His Glu Pro Cys
    690                 695                 700
Ser His Gly Ile Cys Tyr Asp Ala Pro Gly Gly Phe Arg Cys Val Cys
705                 710                 715                 720
Glu Pro Gly Trp Ser Gly Pro Arg Cys Ser Gln Ser Leu Ala Arg Asp
                725                 730                 735
Ala Cys Glu Ser Gln Pro Cys Arg Ala Gly Gly Thr Cys Ser Ser Asp
            740                 745                 750
Gly Met Gly Phe His Cys Thr Cys Pro Pro Gly Val Gln Gly Arg Gln
        755                 760                 765
```

-continued

```
Cys Glu Leu Leu Ser Pro Cys Thr Pro Asn Pro Cys Glu His Gly Gly
        770                 775                 780

Arg Cys Glu Ser Ala Pro Gly Gln Leu Pro Val Cys Ser Cys Pro Gln
785                 790                 795                 800

Gly Trp Gln Gly Pro Arg Cys Gln Gln Asp Val Asp Glu Cys Ala Gly
                805                 810                 815

Pro Ala Pro Cys Gly Pro His Gly Ile Cys Thr Asn Leu Ala Gly Ser
            820                 825                 830

Phe Ser Cys Thr Cys His Gly Gly Tyr Thr Gly Pro Ser Cys Asp Gln
        835                 840                 845

Asp Ile Asn Asp Cys Asp Pro Asn Pro Cys Leu Asn Gly Gly Ser Cys
    850                 855                 860

Gln Asp Gly Val Gly Ser Phe Ser Cys Ser Cys Leu Pro Gly Phe Ala
865                 870                 875                 880

Gly Pro Arg Cys Ala Arg Asp Val Asp Glu Cys Leu Ser Asn Pro Cys
                885                 890                 895

Gly Pro Gly Thr Cys Thr Asp His Val Ala Ser Phe Thr Cys Thr Cys
            900                 905                 910

Pro Pro Gly Tyr Gly Gly Phe His Cys Glu Gln Asp Leu Pro Asp Cys
        915                 920                 925

Ser Pro Ser Ser Cys Phe Asn Gly Gly Thr Cys Val Asp Gly Val Asn
    930                 935                 940

Ser Phe Ser Cys Leu Cys Arg Pro Gly Tyr Thr Gly Ala His Cys Gln
945                 950                 955                 960

His Glu Ala Asp Pro Cys Leu Ser Arg Pro Cys Leu His Gly Gly Val
                965                 970                 975

Cys Ser Ala Ala His Pro Gly Phe Arg Cys Thr Cys Leu Glu Ser Phe
            980                 985                 990

Thr Gly Pro Gln Cys Gln Thr Leu Val Asp Trp Cys Ser Arg Gln Pro
        995                1000                1005

Cys Gln Asn Gly Gly Arg Cys Val Gln Thr Gly Ala Tyr Cys Leu Cys
    1010                1015                1020

Pro Pro Gly Trp Ser Gly Arg Leu Cys Asp Ile Arg Ser Leu Pro Cys
1025                1030                1035                1040

Arg Glu Ala Ala Ala Gln Ile Gly Val Arg Leu Glu Gln Leu Cys Gln
                1045                1050                1055

Ala Gly Gly Gln Cys Val Asp Glu Asp Ser Ser His Tyr Cys Val Cys
            1060                1065                1070

Pro Glu Gly Arg Thr Gly Ser His Cys Glu Gln Glu Val Asp Pro Cys
        1075                1080                1085

Leu Ala Gln Pro Cys Gln His Gly Gly Thr Cys Arg Gly Tyr Met Gly
    1090                1095                1100

Gly Tyr Met Cys Glu Cys Leu Pro Gly Tyr Asn Gly Asp Asn Cys Glu
1105                1110                1115                1120

Asp Asp Val Asp Glu Cys Ala Ser Gln Pro Cys Gln His Gly Gly Ser
                1125                1130                1135

Cys Ile Asp Leu Val Ala Arg Tyr Leu Cys Ser Cys Pro Pro Gly Thr
            1140                1145                1150

Leu Gly Val Leu Cys Glu Ile Asn Glu Asp Asp Cys Gly Pro Gly Pro
        1155                1160                1165

Pro Leu Asp Ser Gly Pro Arg Cys Leu His Asn Gly Thr Cys Val Asp
    1170                1175                1180

Leu Val Gly Gly Phe Arg Cys Thr Cys Pro Pro Gly Tyr Thr Gly Leu
```

-continued

```
           1185                1190                1195                1200

Arg Cys Glu Ala Asp Ile Asn Glu Cys Arg Ser Gly Ala Cys His Ala
                      1205                1210                1215

Ala His Thr Arg Asp Cys Leu Gln Asp Pro Gly Gly Phe Arg Cys
                      1220                1225                1230

Leu Cys His Ala Gly Phe Ser Gly Pro Arg Cys Gln Thr Val Leu Ser
                  1235                1240                1245

Pro Cys Glu Ser Gln Pro Cys Gln His Gly Gly Gln Cys Arg Pro Ser
                  1250                1255                1260

Pro Gly Pro Gly Gly Gly Leu Thr Phe Thr Cys His Cys Ala Gln Pro
      1265                1270                1275                1280

Phe Trp Gly Pro Arg Cys Glu Arg Val Ala Arg Ser Cys Arg Glu Leu
                      1285                1290                1295

Gln Cys Pro Val Gly Val Pro Cys Gln Gln Thr Pro Arg Gly Pro Arg
                      1300                1305                1310

Cys Ala Cys Pro Pro Gly Leu Ser Gly Pro Ser Cys Arg Ser Phe Pro
                  1315                1320                1325

Gly Ser Pro Pro Gly Ala Ser Asn Ala Ser Cys Ala Ala Ala Pro Cys
                  1330                1335                1340

Leu His Gly Gly Ser Cys Arg Pro Ala Pro Leu Ala Pro Phe Phe Arg
      1345                1350                1355                1360

Cys Ala Cys Ala Gln Gly Trp Thr Gly Pro Arg Cys Glu Ala Pro Ala
                      1365                1370                1375

Ala Ala Pro Glu Val Ser Glu Pro Arg Cys Pro Arg Ala Ala Cys
                      1380                1385                1390

Gln Ala Lys Arg Gly Asp Gln Arg Cys Asp Arg Glu Cys Asn Ser Pro
                  1395                1400                1405

Gly Cys Gly Trp Asp Gly Gly Asp Cys Ser Leu Ser Val Gly Asp Pro
                  1410                1415                1420

Trp Arg Gln Cys Glu Ala Leu Gln Cys Trp Arg Leu Phe Asn Asn Ser
      1425                1430                1435                1440

Arg Cys Asp Pro Ala Cys Ser Ser Pro Ala Cys Leu Tyr Asp Asn Phe
                      1445                1450                1455

Asp Cys His Ala Gly Gly Arg Glu Arg Thr Cys Asn Pro Val Tyr Glu
                      1460                1465                1470

Lys Tyr Cys Ala Asp His Phe Ala Asp Gly Arg Cys Asp Gln Gly Cys
                  1475                1480                1485

Asn Thr Glu Glu Cys Gly Trp Asp Gly Leu Asp Cys Ala Ser Glu Val
                  1490                1495                1500

Pro Ala Leu Leu Ala Arg Gly Val Leu Val Leu Thr Val Leu Leu Pro
      1505                1510                1515                1520

Pro Glu Glu Leu Leu Arg Ser Ser Ala Asp Phe Leu Gln Arg Leu Ser
                      1525                1530                1535

Ala Ile Leu Arg Thr Ser Leu Arg Phe Arg Leu Asp Ala His Gly Gln
                      1540                1545                1550

Ala Met Val Phe Pro Tyr His Arg Pro Ser Pro Gly Ser Glu Pro Arg
                  1555                1560                1565

Ala Arg Arg Glu Leu Ala Pro Glu Val Ile Gly Ser Val Val Met Leu
            1570                1575                1580

Glu Ile Asp Asn Arg Leu Cys Leu Gln Ser Pro Glu Asn Asp His Cys
      1585                1590                1595                1600

Phe Pro Asp Ala Gln Ser Ala Ala Asp Tyr Leu Gly Ala Leu Ser Ala
                      1605                1610                1615
```

-continued

Val Glu Arg Leu Asp Phe Pro Tyr Pro Leu Arg Asp Val Arg Gly Glu
            1620                1625                1630

Pro Leu Glu Pro Pro Glu Pro Ser Val Pro Leu Leu Pro Leu Leu Val
1635                1640                1645

Ala Gly Ala Val Leu Leu Leu Val Ile Leu Val Leu Gly Val Met Val
    1650                1655                1660

Ala Arg Arg Lys Arg Glu His Ser Thr Leu Trp Phe Pro Glu Gly Phe
1665                1670                1675                1680

Ser Leu His Lys Asp Val Ala Ser Gly His Lys Gly Arg Arg Glu Pro
            1685                1690                1695

Val Gly Gln Asp Ala Leu Gly Met Lys Asn Met Ala Lys Gly Glu Ser
            1700                1705                1710

Leu Met Gly Glu Val Ala Thr Asp Trp Met Asp Thr Glu Cys Pro Glu
        1715                1720                1725

Ala Lys Arg Leu Lys Val Glu Glu Pro Gly Met Gly Ala Glu Glu Ala
    1730                1735                1740

Val Asp Cys Arg Gln Trp Thr Gln His His Leu Val Ala Ala Asp Ile
1745                1750                1755                1760

Arg Val Ala Pro Ala Met Ala Leu Thr Pro Pro Gln Gly Asp Ala Asp
            1765                1770                1775

Ala Asp Gly Met Asp Val Asn Val Arg Gly Pro Asp Gly Phe Thr Pro
            1780                1785                1790

Leu Met Leu Ala Ser Phe Cys Gly Gly Ala Leu Glu Pro Met Pro Thr
        1795                1800                1805

Glu Glu Asp Glu Ala Asp Asp Thr Ser Ala Ser Ile Ile Ser Asp Leu
    1810                1815                1820

Ile Cys Gln Gly Ala Gln Leu Gly Ala Arg Thr Asp Arg Thr Gly Glu
1825                1830                1835                1840

Thr Ala Leu His Leu Ala Ala Arg Tyr Ala Arg Ala Asp Ala Ala Lys
            1845                1850                1855

Arg Leu Leu Asp Ala Gly Ala Asp Thr Asn Ala Gln Asp His Ser Gly
            1860                1865                1870

Arg Thr Pro Leu His Thr Ala Val Thr Ala Asp Ala Gln Gly Val Phe
        1875                1880                1885

Gln Ile Leu Ile Arg Asn Arg Ser Thr Asp Leu Asp Ala Arg Met Ala
    1890                1895                1900

Asp Gly Ser Thr Ala Leu Ile Leu Ala Ala Arg Leu Ala Val Glu Gly
1905                1910                1915                1920

Met Val Glu Glu Leu Ile Ala Ser His Ala Asp Val Asn Ala Val Asp
            1925                1930                1935

Glu Leu Gly Lys Ser Ala Leu His Trp Ala Ala Ala Val Asn Asn Val
            1940                1945                1950

Glu Ala Thr Leu Ala Leu Leu Lys Asn Gly Ala Asn Lys Asp Met Gln
        1955                1960                1965

Asp Ser Lys Glu Glu Thr Pro Leu Phe Leu Ala Ala Arg Glu Gly Ser
    1970                1975                1980

Tyr Glu Ala Ala Lys Leu Leu Leu Asp His Phe Ala Asn Arg Glu Ile
1985                1990                1995                2000

Thr Asp His Leu Asp Arg Leu Pro Arg Asp Val Ala Gln Glu Arg Leu
            2005                2010                2015

His Gln Asp Ile Val Arg Leu Leu Asp Gln Pro Ser Gly Pro Arg Ser
            2020                2025                2030

-continued

```
Pro Pro Gly Pro His Gly Leu Gly Pro Leu Leu Cys Pro Pro Gly Ala
        2035                2040                2045

Phe Leu Pro Gly Leu Lys Ala Ala Gln Ser Gly Ser Lys Lys Ser Arg
    2050                2055                2060

Arg Pro Pro Gly Lys Ala Gly Leu Gly Pro Gln Gly Pro Arg Gly Arg
2065                2070                2075                2080

Gly Lys Lys Leu Thr Leu Ala Cys Pro Gly Pro Leu Ala Asp Ser Ser
            2085                2090                2095

Val Thr Leu Ser Pro Val Asp Ser Leu Asp Ser Pro Arg Pro Phe Gly
            2100                2105                2110

Gly Pro Pro Ala Ser Pro Gly Gly Phe Pro Leu Glu Gly Pro Tyr Ala
        2115                2120                2125

Ala Ala Thr Ala Thr Ala Val Ser Leu Ala Gln Leu Gly Gly Pro Gly
    2130                2135                2140

Arg Ala Gly Leu Gly Arg Gln Pro Pro Gly Gly Cys Val Leu Ser Leu
2145                2150                2155                2160

Gly Leu Leu Asn Pro Val Ala Val Pro Leu Asp Trp Ala Arg Leu Pro
            2165                2170                2175

Pro Pro Ala Pro Pro Gly Pro Ser Phe Leu Leu Pro Leu Ala Pro Gly
        2180                2185                2190

Pro Gln Leu Leu Asn Pro Gly Thr Pro Val Ser Pro Gln Glu Arg Pro
            2195                2200                2205

Pro Pro Tyr Leu Ala Val Pro Gly His Gly Glu Glu Tyr Pro Val Ala
        2210                2215                2220

Gly Ala His Ser Ser Pro Pro Lys Ala Arg Phe Leu Arg Val Pro Ser
2225                2230                2235                2240

Glu His Pro Tyr Leu Thr Pro Ser Pro Glu Ser Pro Glu His Trp Ala
            2245                2250                2255

Ser Pro Ser Pro Pro Ser Leu Ser Asp Trp Ser Glu Ser Thr Pro Ser
            2260                2265                2270

Pro Ala Thr Ala Thr Gly Ala Met Ala Thr Thr Thr Gly Ala Leu Pro
        2275                2280                2285

Ala Gln Pro Leu Pro Leu Ser Val Pro Ser Ser Leu Ala Gln Ala Gln
    2290                2295                2300

Thr Gln Leu Gly Pro Gln Pro Glu Val Thr Pro Lys Arg Gln Val Leu
2305                2310                2315                2320

Ala

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 3
ctgcaggtga ggggc                                                        15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 4
```
cccacacagc ccccc                                                15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 5
ctgcctgtga gtgcc                                                15

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 6
gcccacaggt gccc                                                 14

<210> SEQ ID NO 7
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 7
tccgaggtga gagg                                                 14

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 8
ccctccaggc cctg                                                 14

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 9
ttcctggtga gtga                                                 14

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 10
cttgttaggg tttg                                                 14

<210> SEQ ID NO 11
<211> LENGTH: 14
<212> TYPE: DNA
<213> ORGANISM: Artificial Sequence

```
<220> FEATURE:
<223> OTHER INFORMATION: Description of Artificial Sequence: primer

<400> SEQUENCE: 11
ggacaggtgg gcac                                                              14

<210> SEQ ID NO 12
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 12
tgccacaggc cagt                                                              14

<210> SEQ ID NO 13
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 13
agactggtga gtgg                                                              14

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 14
cttcccaggc ctcc                                                              14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 15
ctatcggtga gggg                                                              14

<210> SEQ ID NO 16
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 16
tccggcaggc gcca                                                              14

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 17
tggcaggtgg gtgg                                                              14
```

<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 18
tgccccaggc ttca                                                    14

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 19
cctcgggtga ggac                                                    14

<210> SEQ ID NO 20
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 20
caccccaggc ttca                                                    14

<210> SEQ ID NO 21
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 21
ccgagggtga ggcg                                                    14

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 22
ccccacaggc tttg                                                    14

<210> SEQ ID NO 23
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 23
ccacaggtgg gacc                                                    14

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 24
gccactaggt gtga                                            14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 25
tcacaggtgg gcaa                                            14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 26
ctccccaggg cccc                                            14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 27
tggcgggtga gggc                                            14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 28
cctgccaggt tccg                                            14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 29
tccagggtgt gtac                                            14

<210> SEQ ID NO 30
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 30
cccaacagga cgtc                                            14

<210> SEQ ID NO 31

```
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 31
ggcaaggtat gccac                                                    15

<210> SEQ ID NO 32
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 32
tacccccagg cccac                                                    15

<210> SEQ ID NO 33
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 33
accccagtga gtgca                                                    15

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 34
gtccgcagac ccat                                                     14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 35
ccccaggtgg gcgg                                                     14

<210> SEQ ID NO 36
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 36
cgctccagct cctg                                                     14

<210> SEQ ID NO 37
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 37
```
tgccaggtgg gtgg                                                         14

<210> SEQ ID NO 38
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 38
ccctccagac gctg                                                         14

<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 39
agatcggtga gtgg                                                         14

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 40
ctttgcaggg gtgc                                                         14

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 41
tgtgaggtaa gggg                                                         14

<210> SEQ ID NO 42
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 42
cactgaagtg tctt                                                         14

<210> SEQ ID NO 43
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 43
cgctgggtat gcca                                                         14

<210> SEQ ID NO 44
<211> LENGTH: 14
<212> TYPE: DNA

```
<213> ORGANISM: Artificial Sequence
<220> FEATURE:
<223> OTHER INFORMATION: Description of Artificial Sequence: primer

<400> SEQUENCE: 44
tcccccaggg gtgc                                                     14

<210> SEQ ID NO 45
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 45
tctcaggtta acct                                                     14

<210> SEQ ID NO 46
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 46
tcgctcaggt cctc                                                     14

<210> SEQ ID NO 47
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 47
gcccaggtag gtgtg                                                    15

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 48 gaccccagc cgttc                                                     15

<210> SEQ ID NO 49
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 49
ttgcaagtga gccc                                                     14

<210> SEQ ID NO 50
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 50
cccaccagcc cggt                                                     14
```

```
<210> SEQ ID NO 51
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 51
gatcgggtga gtgac                                                       15

<210> SEQ ID NO 52
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 52
tccctgcagc tcggt                                                       15

<210> SEQ ID NO 53
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 53
tgcggggtgc ggcc                                                        14

<210> SEQ ID NO 54
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 54
tgctcttagg ggagc                                                       15

<210> SEQ ID NO 55
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 55
catgaagtga gaac                                                        14

<210> SEQ ID NO 56
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 56
tccgccagga acat                                                        14

<210> SEQ ID NO 57
<211> LENGTH: 14
<212> TYPE: DNA
<213> ORGANISM: Artificial Sequence
<220> FEATURE:
```

```
<223> OTHER INFORMATION: Description of Artificial Sequence: primer

<400> SEQUENCE: 57
ctaaaggtac tgcc                                                        14

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 58
cccctccagg tagag                                                       15

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 59
gcccaggtca gtgac                                                       15

<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 60
ccctgcagat ggct                                                        14

<210> SEQ ID NO 61
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 61
ttccaggtga gata                                                        14

<210> SEQ ID NO 62
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 62
tgtcctagat tctc                                                        14

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 63
agcttggtag gttg                                                        14
```

```
<210> SEQ ID NO 64
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 64
ccctccaggg aaat                                                         14

<210> SEQ ID NO 65
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 65
agcaaggtga gccc                                                         14

<210> SEQ ID NO 66
<211> LENGTH: 14
<212> TYPE: DNA
<213> ORGANISM: Artificial Sequence
<220> FEATURE:
<223> OTHER INFORMATION: Description of Artificial Sequence: primer

<400> SEQUENCE: 66 cccccagga ggag                                                          14

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 67
aaggagggag gagggag                                                      18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 68
tgggggttct tgcactcc                                                     18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 69
ggttcctgcc tcccatga                                                     18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: primer
```

```
<400> SEQUENCE: 70
tcctccacct tccttcac                                                 18

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 71
acacacaggg cccactggt                                                19

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 72
tgtgctgccc aaccaagcca                                               20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 73
actgaccaca cccccgacta                                               20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 74
tagtcggggg tgtggtcagt                                               20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 75
tcatccacgt cgcttcggca                                               20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 76
atggacgctt cctctgctc                                                19

<210> SEQ ID NO 77
<211> LENGTH: 20
```

```
<212> TYPE: DNA
<213> ORGANISM: Artificial Sequence
<220> FEATURE:
<223> OTHER INFORMATION: Description of Artificial Sequence: primer

<400> SEQUENCE: 77
acatagtggc cctgtgtagc                                              20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 78
atggacgctt cctctgctcc                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 79
cctctgactc tcctgagtag                                              20

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 80
tgaccatcct tgcccccctt                                              19

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 81
ctggcctgtg gcacacagat                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 82
tggactgctg catctgtgtg                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 83
```

-continued

| | |
|---|---|
| acacgcctgt ggcacagtca | 20 |

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 84

| | |
|---|---|
| gagctgcagt cagaatatcg | 20 |

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 85

| | |
|---|---|
| atccatggct ccctgcagag | 20 |

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 86

| | |
|---|---|
| cagagcagga agatctgcct | 20 |

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 87

| | |
|---|---|
| cattcacaga cgacggagct | 20 |

<210> SEQ ID NO 88
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 88

| | |
|---|---|
| atcgcactcc atccggca | 18 |

<210> SEQ ID NO 89
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 89

| | |
|---|---|
| acccacctgc catacaga | 18 |

<210> SEQ ID NO 90
<211> LENGTH: 20
<212> TYPE: DNA
<213> ORGANISM: Artificial Sequence

```
<220> FEATURE:
<223> OTHER INFORMATION: Description of Artificial Sequence: primer

<400> SEQUENCE: 90
cgttcacacc atagggtagc                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 91 cccctteccca gacatgtctt                                             20

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 92
cttgtcggac tgtcattgg                                               19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 93
gtgtactgct ctcaccctt                                               19

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 94
attggtccga ggcctcactt                                              20

<210> SEQ ID NO 95
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 95
acctggctct cgcagcgtgt                                              20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 96
ccattcccaa ccctctgtg                                               20
```

```
<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 97
tgcctgtgct cctggctaca                                                    20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 98
tggccactcc atgccatgtt                                                    20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 99
tctcatggca gccacttgcc                                                    20

<210> SEQ ID NO 100
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 100
atgagtgtgc ttccagccca                                                    20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 101
gcagtgtctg aggctgagaa                                                    20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 102
tccctggcct gactaccttc                                                    20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: primer
```

```
<400> SEQUENCE: 103
ctgcagaggg aaggtgaggt                                              20

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 104
aaggctatcc tgcttcc                                                 17

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 105
gaggaggagg gaagagaa                                                18

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 106
aggatgtgga cgagtgtgct                                              20

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 107
gcttaatgac tgtgttcc                                                18

<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 108
tcagactggg ctaatggggg                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 109
tcgcagtgga agcctccgta                                              20

<210> SEQ ID NO 110
```

```
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 110
gatgtggatg agtgcctgag                                                  20

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 111
gtcctgctct tcaagcaga                                                   19

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 112
gatcctccct cccactcctt                                                  20

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 113
aggtccccag taactcca                                                    18

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 114
actgactcta agtgcttccc                                                  20

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 115
agcaggaggt acgtgcatga                                                  20

<210> SEQ ID NO 116
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 116
```

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 117
acctcctctt ccctctcct                                                  19

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 118
tctgtgtccc actaagctga                                                 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 119
caagaggaaa tgaagacagc                                                 20

<210> SEQ ID NO 120
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 120
ttcctcttga ccaccctcg                                                  20

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 121
tggcaggcac ctgagcgaca                                                 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 122
caggatacac tggtttgcgc                                                 20

<210> SEQ ID NO 123
<211> LENGTH: 20
<212> TYPE: DNA

[line above: tgttcctgtg ccactctcct    20]

```
<213> ORGANISM: Artificial Sequence
<220> FEATURE:
<223> OTHER INFORMATION: Description of Artificial Sequence: primer

<400> SEQUENCE: 123
tgccacgtta tggatcagcc                                              20

<210> SEQ ID NO 124
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 124
gatctacatg ctcccgctcg                                              20

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 125
tactcctcct ccataggccg                                              20

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 126
cgttctgggg tccgcgtt                                                18

<210> SEQ ID NO 127
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 127
aagcgcagcg gaagaagggc                                              20

<210> SEQ ID NO 128
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 128
gcccttcttc cgctgcgctt                                              20

<210> SEQ ID NO 129
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 129
actgcagcgc ctcgcattgc                                              20
```

<210> SEQ ID NO 130
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 130
ctgcgaccgc gagtgcaaca                                              20

<210> SEQ ID NO 131
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 131
atagacagac ggatcgat                                                18

<210> SEQ ID NO 132
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 132
ctctctgcct caccctt                                                 17

<210> SEQ ID NO 133
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 133
gctggaacgc agtagct                                                 17

<210> SEQ ID NO 134
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 134
tgctcacagt gctgctg                                                 17

<210> SEQ ID NO 135
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 135
cacggctttt ccaggtg                                                 17

<210> SEQ ID NO 136
<211> LENGTH: 17
<212> TYPE: DNA
<213> ORGANISM: Artificial Sequence
<220> FEATURE:

<223> OTHER INFORMATION: Description of Artificial Sequence: primer

<400> SEQUENCE: 136
tttgagccct ctggtcc                                              17

<210> SEQ ID NO 137
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 137
aagagcagga agcagag                                              17

<210> SEQ ID NO 138
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 138
tccctctgct tcctgctctt                                           20

<210> SEQ ID NO 139
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 139
tcacaaggtc cccgtagtca                                           20

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 140
ctcacatccc ctcttcccat                                           20

<210> SEQ ID NO 141
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 141
atcacgccca tcatccactg                                           20

<210> SEQ ID NO 142
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 142
cagcaccaaa gggtg                                                15

```
<210> SEQ ID NO 143
<211> LENGTH: 15
<212> TYPE: DNA
<213> ORGANISM: Artificial Sequence
<220> FEATURE:
<223> OTHER INFORMATION: Description of Artificial Sequence: primer

<400> SEQUENCE: 143
catccctttg ggagg                                                    15

<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 144
atggcttcac cccgctaatg                                               20

<210> SEQ ID NO 145
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 145
agccaggtgc aaagcagtct                                               20

<210> SEQ ID NO 146
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 146
tcagcttggg gcacggactg                                               20

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 147
gcatcggctg tgacagctgt                                               20

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 148
tgttcctgcc atgacccct                                                19

<210> SEQ ID NO 149
<211> LENGTH: 20
<212> TYPE: DNA
<213> ORGANISM: Artificial Sequence
<220> FEATURE:
<223> OTHER INFORMATION: Description of Artificial Sequence: primer
```

<400> SEQUENCE: 149
caggtgacac taacccagtc                                                20

<210> SEQ ID NO 150
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 150
tcctgacctc tctcccttc                                                 20

<210> SEQ ID NO 151
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 151
aatggcgctg tgccactgct                                                20

<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 152
gctactgtta gctggggttt                                                20

<210> SEQ ID NO 153
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 153
tgatccagca agcgcacgat                                                20

<210> SEQ ID NO 154
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 154
tcaccgacca cctggaca                                                  18

<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 155
accaagctgt gccagaga                                                  18

<210> SEQ ID NO 156
<211> LENGTH: 18

```
<212> TYPE: DNA
<213> ORGANISM: Artificial Sequence
<220> FEATURE:
<223> OTHER INFORMATION: Description of Artificial Sequence: primer

<400> SEQUENCE: 156
tccaagaaga gcaggagg                                                   18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 157
accaagctgt gccagaga                                                   18

<210> SEQ ID NO 158
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 158
cagtgtctct ggcacagctt                                                 20

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 159
tcctgggact gccaggtaa                                                  19

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 160
agctgctcaa cccaggga                                                   18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 161
gtggattcgg accagtct                                                   18

<210> SEQ ID NO 162
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 162
```

```
gaatccctg agcact                                                          16

<210> SEQ ID NO 163
<211> LENGTH: 16
<212> TYPE: DNA
<213> ORGANISM: Artificial Sequence
<220> FEATURE:
<223> OTHER INFORMATION: Description of Artificial Sequence: primer

<400> SEQUENCE: 163
ctaagaactg acgagc                                                         16
```

GENE INVOLVED IN CADASIL, METHOD OF DIAGNOSIS AND THERAPEUTIC APPLICATION

The present invention relates to the demonstration of the involvement of the Notch3 protein in CADASIL thus allowing in particular a diagnosis of a predisposition to certain neurological disorders, in particular CADASIL, and models which make it possible to test the therapies possible for this type of pathology.

CADASIL or "Cerebral Autosomal Dominant Arteriopathy with Subcortical Infarcts and Leukoencephalopathy" has recently been identified as a cause of cerebral attacks and of dementia whose main characteristics include recidivous subcortical infarcts, migraines and a vascular dementia, in association with MRI images objectivizing diffuse abnormalities of the cerebral white substance.

An anatomicopathological examination shows multiple small deep cerebral infarcts, a leukoencephalopathy and a nonatherosclerotic and nonamyloid angiopathy involving essentially the small cerebral arteries.

As its name indicates, CADASIL is a hereditary disease with a dominant autosomal character. For more information, there may be found in particular a study of the clinical spectrum of CADASIL in H. Chabriat et al., The Lancet, Vol. 346, Oct. 7, 1995.

This highly incapacitating and very often lethal disease has probably remained so far largely undiagnosed as such; the study of about one hundred families since 1993 shows that erroneous diagnoses were most often given to the patient (multiple sclerosis, Alzheimer's disease and the like). Current studies would tend to demonstrate that it is a condition which is much more widespread than what was thought during its discovery.

The research studies currently pursued have the objective of identifying diagnostic tools for the disease and, by virtue, in particular of the models and the possibilities offered by genetic engineering, of developing a possible substitute therapy.

The gene involved in CADASIL has been localized on chromosome 19 and a finer localization is in particular mentioned in two patent applications with the same inventors.

It has now been possible to identify the gene involved in CADASIL which is the Notch3 gene.

The demonstration of the involvement of Notch3 in CADASIL has been possible given the previous limits which had been mentioned especially in the patent applications in question, the first interval (size 14 cM) was D19S221-D19S215 (first patent application), and then the second interval (size 2 cM) was D19S226-D19S199 (second patent application). The region of interest was cloned into a BAC and YAC contig (continuous nucleotide sequence) and its size was estimated at 800 kb. Analysis of this region with the aid of restriction enzymes showed a very high density of NotI, EagI and SacII sites which suggested the presence of numerous genes. Among the numerous transcripts identified by cDNA selection, one transcript showed a very strong homology with a sequence situated at the coding 5' end of the mouse gene Notch3. Since other analytical factors seemed to corroborate this presence of the Notch3 gene in this situation, the latter was considered to be a good candidate gene by its position in the interval of interest.

The comparative studies carried out on known CADASIL families in comparison with healthy subjects have made it possible to identify mutations on this Notch3 gene in a large number of CADASIL subjects whereas such mutations were not observed on the healthy subjects analyzed. Since, finally, it has been possible to demonstrate the cosegregation of these mutations with the disease phenotype within effected families, the involvement of the Notch3 gene in CADASIL became incontestable.

All the point mutations observed lead to the creation or to the disappearance of a cysteine in one of the EGF domains of this protein. These mutations are clustered for a large part of them into the first six EGFs. The clustering of the mutations is certainly important in diagnostic terms especially for the "sequential" search for these mutations.

Moreover, all these mutations lead to the presence of an odd number of cysteines in one of the EGFs (either seven, or five cysteines) instead of the six cysteines normally present. These mutations could thus result in the formation of either intra- or intermolecular (and in this case in the formation of homo- or heterodimers) aberrant disulfide bridges.

The role of a normal or abnormal dimerization in the functioning of receptors, in particular their activation, is well known.

The Notch genes have been known for a very long time, especially in drosophila and their equivalent is known in vertebrates, in particular in mice. Its English name "notch" comes from the fact that some mutations of this gene produce a notch in the wings of flies. The article by Spyros Artavanis-Tskanas et al., Science 268, 225 (1995) as well as the references which it contains indicate that the Notch proteins are essentially involved, especially in drosophila, in the specification of the cellular destiny during development, and although the protein is always expressed in adult organisms, its functions in the latter remain unknown. More precisely, it appears that the product of the Notch3 gene, hereinafter "Notch3 protein", is a cell receptor which controls a cascade of cellular events and whose mutation necessarily leads to greater or lesser disruptions in this cascade which may lead to many other neurological, especially cerebrovascular, disorders.

It should be recalled that, while in the text which follows there is interest more particularly in neurological disorders, in particular cerebrovascular-type disorders and most particularly CADASIL, it is probable, given the function of the cell receptor for the product of the Notch3 gene, that impairment of this receptor can lead to a disorganization of its interaction with various ligands but also with the various partners involved in the transduction cascade. Account should be taken, in addition, of the fact that the Notch3 protein might have other functions which have not yet been demonstrated. Under these conditions, it is highly probable that conditions exhibiting similarities with CADASIL may also be involved in the case of a mutation in the Notch3 gene.

Among the relevant diseases, there may be mentioned the sporadic forms of CADASIL, that is to say which occur without a family history but following a neomutation. Notch3 might moreover be involved in other conditions which may be classified into different groups:

Migraine and Hemiplegic Migraine

It was shown that at least one of the genes involved in familial hemiplegic migraine (FHM), the dominant autosomal form of migraine with aura, was located in the same region of chromosome 19 as the CADASIL gene. It should be noted that more than 30% of patients suffering from CADASIL, a condition characterized by the repeated onset of cerebrovascular accidents and of a vascular dementia, suffered from migraine with aura. However, the latter is observed in only about 5% of the population; it is this observation which led to testing the involvement of the CADASIL gene in the mechanisms of this condition. The involvement of this gene in a form of migraine with or without aura was of considerable diagnostic and therapeutic interest because of the frequency of migraine with aura and of migraine without aura in the general population.

Other Vascular (Cerebral Infarct) and/or Dementia Pathologies of Unknown Etiology This group corresponds to a very large number of patients in neurology, psychiatric and internal medicine departments and it is everything to do reasonable to think that Notch3 or a partner in this signaling pathway may be involved in these conditions for the reasons stated above.

Familial Paroxytic Ataxia

The situation is the same as for FHM. A gene responsible for this condition has been located in the same region of chromosome 19 and Notch3 could be implicated in this condition.

Moreover, the mutations of this gene are responsible for developmental abnormalities which are well known in other species as well as for neoplastic-type pathologies. Malformative and/or neoplastic syndromes in which there may be demonstrated a rearrangement of the region which contains this gene might be major candidates for the search for an involvement of this gene in their physiopathology.

These disorders may be grouped under the name of "disorders linked to the Notch3 receptor".

In some cases, this may involve disorders having a multigenic origin but in which the modifications of Notch3 might contribute to the onset of the pathology or to its worsening.

The present invention relates, first of all, to an isolated nucleotide sequence, characterized in that it is chosen from:

a) the sequences encoding the human Notch3 protein and its allelic variants,
b) the sequences encoding a fragment of these proteins and having at least 10 bases,
c) the human Notch3 genomic sequences and its alleles,
d) the sequences exhibiting at least 80%, and preferably at least 90%, homology with the sequences (a) and (c),
e) the fragments of the sequences (c) or (d) having at least 10 bases,
f) the sequences which hybridize with a sequence of (a) to (e).

It should be understood that the present invention does not relate to the genomic nucleotide sequences in their natural chromosomal environment, that is to say in the natural state; they are sequences which have been isolated, that is to say that they were collected directly or indirectly, for example by copying (cDNA), their environment having been at least partially modified.

Thus, this may also involve both cDNA and genomic DNA which is partially modified or carried by sequences which are at least partially different from the sequences carrying them naturally.

These sequences may also be described as being "non-natural".

"Nucleic sequence" is understood to mean a natural isolated, or synthetic, fragment of DNA and/or RNA designating a precise linkage of nucleotides, modified or otherwise, making it possible to define a fragment, a segment or a region of a nucleic acid.

"Allelic variant" of the protein is understood to mean all the mutated proteins and the polymorphisms which may exist in a human being, which are obtained in particular by truncation, substitution, deletion or addition of amino acid residues, as well as the artificial variants.

According to the invention, the nucleic sequence fragments may in particular encode domains of the protein or may be used as probe or as primer in methods of detection, identification or amplification. These fragments have a minimum size of 10 bases and fragments of 20 bases, preferably 30 bases, will be preferred.

According to the invention, the homology is solely of the statistical type; it means that the sequences exhibit at least 80%, and preferably 90%, of nucleotides in common.

The hybridization conditions should make it possible, according to the invention, to ensure at least 95% homology.

More particularly, the present invention relates to a nucleotide sequence chosen from:

a) the sequences encoding a polypeptide comprising the amino acids according to the sequence in FIG. 1,
b) the nucleic sequences corresponding to FIG. 1,
c) a fragment of a sequence according to (a) or (b) containing at least 10 bases, and
d) a sequence which contains, relative to the sequences (a), (b) or (c), at most 20 partial mutations.

FIG. 1 represents the sequences of Notch3 as were sequenced on a normal genome.

Figure 3:
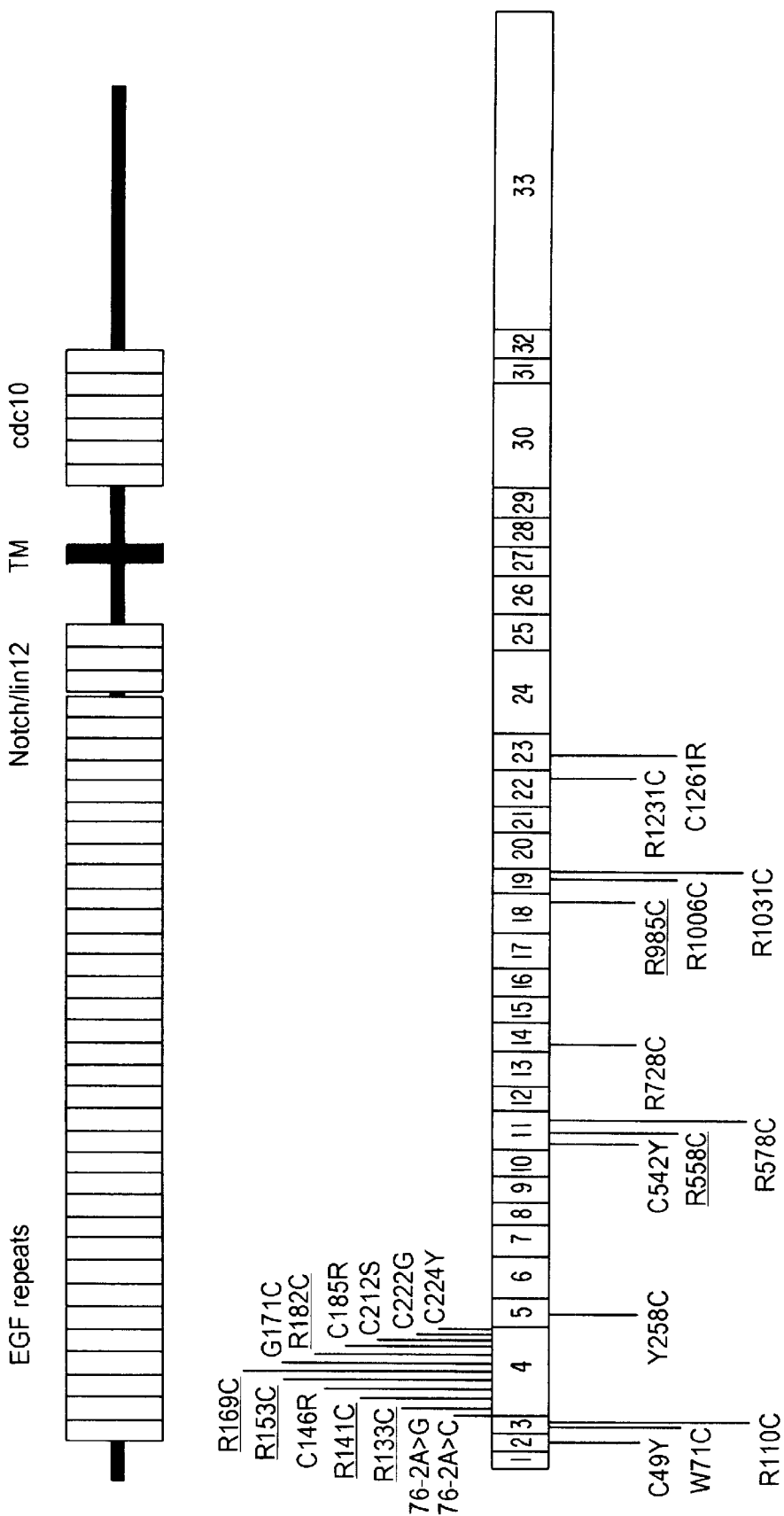

The sequences are identified by references which make it possible to position them relative to each other using FIG. 3.

As regards the special remarks on (a), (b), (c) and (d), the previous remarks apply.

The invention also relates to the fragments of these sequences, in particular sequences encoding polypeptides which have retained all or part of the activity of the Notch3 protein.

Among the particularly advantageous sequences, there may be mentioned those encoding domains or combinations of domains of the Notch3 protein, that is to say the sequences:

"EGF" repeats
"Notch/lin12" repeats
"cdc10/SW16" repeats
or the transmembrane sequence.

Among the advantageous sequences are in particular the sequence encoded by the second transcript which will be described in the text which follows, the said transcript having an estimated size of between 1.3 and 2.4 kb.

These sequences may be identified with reference in particular to FIG. 2 which schematically represents the organization of Notch3.

These partial sequences can be used for numerous applications, as described below, especially for preparing Notch-type or different types of protein constructs, but also for preparing, for example, truncated Notch-like proteins which will serve as lure for the Notch3 ligand or as agonist for the protein.

It is also possible to envisage using these protein sequences for their intrinsic effects; thus, the EGF domains are present in other proteins, especially other receptors; reference may be made for example to Iain D. Campbell, Current Biology, 3: 385–392 (1993) for other applications of the EGF sequences in question.

While the sequences described are in general normal sequences, the invention also relates to the mutated sequences insofar as they contain at least one point mutation and preferably less than 20 mutations in total.

Preferably, the present invention relates to the nucleotide sequences in which the point mutations are not silent, that is to say that they lead to a modification of the amino acid encoded relative to the normal sequence. Still more preferably, these mutations affect amino acids which structure the Notch3 protein or the corresponding fragments thereof, that is to say in particular the mutations which suppress the cysteines or, on the contrary, which make them appear, but also the mutations which change the character of the protein, either from the charge point of view, or from the hydrophobicity point of view.

The present invention also relates to the mutations which may occur in the promoter and/or regulatory sequences of the human Notch3 gene, which may have effects on the expression of the protein.

Examples of such mutations will be described in the text which follows.

In general, the present invention relates to both the normal Notch3 protein and the mutated Notch3 proteins, as well as to their fragments and to the corresponding DNA and RNA sequences, that is to say the alleles.

It should be noted that the Northern blot study of the expression of this gene in human tissues reveals two transcripts. One having a size estimated at 7.5–9.5 kb is present in all the tissues tested; the other, whose size is between 1.3 and 2.4 kb, is detected only in some parts of the central nervous system. The present invention relates to these two transcripts.

Among the nucleotide fragments, there may be mentioned the intron genomic sequences of the Notch3 gene and more particularly the joining sequences between the introns and the exons, especially as are represented in Table A; and finally, the present invention relates to all the primers which may be deduced from the preceding nucleotide sequences and which may make it possible to detect them using an amplification method such as the PCR method, especially those presented in Table B.

The present invention also relates to the nucleotide sequences which may contain nonnatural nucleotides, especially sulfur-containing nucleotides for example or having an α or β structure.

Finally, the present invention of course relates to both the DNA and RNA sequences, as well as the corresponding double-stranded DNAs.

As will be described below for some applications, it may be necessary to provide for mixed constructs, protein/DNA/chemical compound, especially the use of intercalating agents for example; it should be understood that such compounds are covered by the patent as containing a sequence according to the invention.

The present invention also relates to the polypeptide or peptide proteins corresponding to the abovementioned sequences, in a nonnatural form, that is to say that they are not taken in their natural environment but obtained by purification from natural sources or obtained by genetic recombination, as will be described below.

The invention also relates to the same polypeptides or proteins obtained by chemical synthesis and capable of containing nonnatural amino acids.

The present invention relates to the recombinant proteins thus obtained both in a glycosylated and nonglycosylated form and capable of having or otherwise the natural tertiary structure.

In particular, the present invention relates to the Notch3 fragments which exhibit an activity similar to the total receptor, especially the soluble part(s) of said receptor corresponding in particular to their extracellular domain. These may be used especially as a lure in a therapy, as will be described below.

The present invention also relates to the cloning and expression vectors containing a nucleotide sequence as described above.

These cloning and expression vectors may contain elements ensuring the expression of the sequence in a host cell, especially promoter sequences and regulatory sequences which are efficient in said cell (see reference below).

The vector in question may be autonomously replicating or intended to ensure the integration of the sequence into the chromosomes of the host cell.

In the case of autonomously replicating systems, depending on the prokaryotic or eukaryotic host cell, plasmid-type systems or viral systems will preferably be used, it being possible for the viral vectors to be especially adenoviruses, poxviruses or herpesviruses. Persons skilled in the art know the technologies which can be used for each of these viruses (see reference below).

When the integration of the sequence into the chromosomes of the host cell is desired, it will be necessary to provide for, on either side of the nucleotide sequence to be integrated, one or more sequences obtained from the host cell in order to bring about the recombination. These are also methods which are widely described in the prior art. It will be possible, for example, to use plasmid or viral type systems; such viruses will be, for example, retroviruses or AAVs (Adeno-Associated Viruses).

The invention also relates to the prokaryotic or eukaryotic cells transformed by a vector as described above, and this being in order to bring about the expression of a natural or mutated Notch3 protein or, for example, of one of its subunits.

As indicated above, the present invention also relates to the proteins, peptides or polypeptides obtained by culturing the cells thus transformed and recovering the protein expressed, it being possible for said recovery to be carried out intracellularly or extracellularly from the culture medium when the vector has been designed to bring about the excretion of the protein via for example a "leader" sequence, the protein being in a pre-protein or preproprotein form. The constructs allowing the secretion of the proteins are known both for prokaryotic systems and eukaryotic systems.

Among the cells which can be used for the production of these proteins, there may of course be mentioned bacterial cells, but also yeast cells, as well as animal cells, in particular mammalian cell cultures, but also insect cells in which methods using baculoviruses for example may be used (see reference below).

The cells thus obtained can make it possible to prepare natural or mutated Notch3 proteins, but also fragments of these proteins, especially polypeptides which may correspond to the different domains in question.

However, the cells transformed as described above may also be used as a model to study the interactions between the Notch gene and its various ligands as well as its influence on the products downstream of the receptor, but in particular they may be used in an application for the selection of products interacting with the natural or mutated Notch3 receptor, as an agonist or an antagonist of this receptor.

This type of cellular model may be produced using genetic engineering techniques. It involves, depending on the type of cells which it is desired to use, cloning the gene in question in its normal form or in its mutated form into an expression vector, whether it is an autonomously replicating vector or an integration vector, said vector containing all the elements allowing the expression of the gene in the cell in question, or the latter having all the elements allowing the expression of the sequence in question.

There are thus obtained eukaryotic or prokaryotic cells expressing the Notch3 protein(s) which, given its characteristics, will be situated like a transmembrane protein whose fine structure will be described in the text which follows, it being possible for said cells to then constitute models which make it possible to test at the same time the interactions of various ligands with the product of the Notch3 protein or to test synthetic chemical products capable of interacting with the product of the Notch3 gene, and this by adding them to the culture medium for said cells.

It should in particular be noted that the products in question may also be products with either antagonist or agonist activity.

The use of cellular models to test pharmaceutical products is well known; here again, there is no need to present this type of model in detail.

Another potential application of the characterization of this gene is the possibility of identifying potential ligands for this protein, either because they have a conserved sequence with human Notch3, or because they interact with Notch3 (affinity methods) or partners for this signaling pathway.

These models may be of the in vitro type, for example cultures of human cells, either in a normal culture, or possibly in the form of an isolated organ, such as for example certain types of vessels which may be transformed in order to cause them to express the desired phenotypes.

The present invention also relates to the organisms, such as animals, in particular mice, expressing the phenotype corresponding to the normal or mutated Notch3 of human origin. Here again, these animals may be used as model animals to test the efficacy of certain pharmaceutical products.

The present invention also relates to the products obtained using the preceding cellular models.

There will thus be obtained, depending on the type of interaction determined, therapeutic compositions characterized in that they contain, as active ingredient, a compound with a pro-Notch3 activity; this may be in particular all or part of a polypeptide as were described above or a vector expressing these same polypeptides, or else chemical or biological compounds having a pro-Notch3 activity, a Notch3-like activity or inducing the production of natural Notch3.

It will also be possible to demonstrate therapeutic compositions in which the active ingredient will have an anti-Notch3 action.

This may involve, here again, modified proteins described above which may play the role of a lure, or anti-Notch3 antibodies, in particular when these antibodies recognize the mutated receptors and will, under these conditions, be able to block the activity of the normal receptor.

This may also involve chemical products having an anti-Notch3 activity, or Notch3 antagonists.

In some cases, the use of some of the Notch3 domains may allow a therapeutic approach blocking the activity of the Notch3 receptor when the latter is mutated using soluble receptors which will serve as lure to the natural ligands; in other cases, it will be possible, by expressing the entire receptor, to provide a replacement therapy using either directly the proteins or fragments thereof, or directly expressing the protein, especially via gene therapy and using the vectors which were described above.

In the context of gene therapy, it is also possible to provide for the use of the sequences of the genes or cDNAs described above as "naked"; this technique was in particular developed by the company Vical; it has shown that it was possible, under these conditions, to express the protein in certain tissues without requiring the use of the support for a viral vector in particular.

Still in the context of gene therapy, it is also possible to provide for the use of cells transformed ex vivo, which cells may then be reimplanted either as such or in systems of the organoid type, as is also known in the state of the art. It is also possible to envisage the use of an agent facilitating targeting of the determined cell type, penetration into the cells or transport to the nucleus.

Among the numerous pharmaceutical compounds which can be used, there should be mentioned more particularly, in addition to the ligands for the Notch3 product, the sense or anti-sense sequences interacting with the normal or mutated Notch3 gene, or interacting on the regulation or expression of these genes, it being also possible for said products to interact downstream of the expression products induced by the Notch3 receptors. The soluble sequences corresponding to Notch3 should furthermore be cited.

There should also be mentioned the monoclonal antibodies blocking the Notch3 receptors, in particular the mutated Notch3 receptors, and/or blocking the corresponding ligands and/or the products induced by said receptors which may therefore have pro or anti activities.

It should be recalled that the monoclonal antibodies directed against the Notch3 receptor may, depending on the epitope recognized, have a pro or anti-Notch3 activity which makes them useable in therapeutic compositions.

Finally, the present invention relates, as was said above, more particularly to the methods of diagnosing a predisposition to neurological conditions, especially of the CADASIL type, or of diseases linked to the Notch3 receptor in a patient, characterized in that the presence of a mutation in Notch3 is determined using a biological sample from said patient by analysis of all or part of a nucleic sequence corresponding to said gene, the presence of at least one such mutation being indicative of a predisposition of said patient to neurological conditions or diseases linked to the Notch3 receptor.

Other diagnostic methods can make it possible to characterize, by means of antibodies, the deposit expected in the basal membrane of the vascular smooth muscle cells, a deposit which might consist of the Notch3 protein itself or one of its cleavage products.

Among the desired mutations, there may be mentioned more particularly the mutations referenced in Table C and FIG. 3.

The nucleic acid sequences may be either genomic DNA, a cDNA or an mRNA.

As was said above, among the neurological disorders which may be demonstrated, there is understood more particularly disorders of the cerebrovascular type and especially CADASIL, but the list of certain disorders which might be linked to an abnormality in the Notch3 receptor has been previously given; among these conditions, there may be mentioned most particularly the potential involvement of Notch3 in migraines with or without aura and dementias of currently unknown etiology.

The diagnostic tools based on the present invention may allow a positive and differential diagnosis in a patient taken in isolation or alternatively a presymptomatic diagnosis in an at-risk subject (family history for example), it is also possible to envisage an antenatal diagnosis.

In addition, the detection of a specific mutation may allow an evolutive diagnosis.

The methods which make it possible to demonstrate the mutation in a gene relative to the natural gene are of course very numerous; they may be carried out by studying the genomic DNA, the cDNA and/or the protein. They can be essentially divided into two large categories, the first type of method is that in which the presence of a mutation is detected by comparing the mutated sequence with the corresponding nonmutated natural sequence, and the second type in which the presence of the mutation is detected indirectly, for example, by detecting the mismatches due to the presence of the mutation.

In both cases, the methods in which all or part of the sequence corresponding to Notch3 is amplified prior to the detection of the mutation will be preferred in general; these amplification methods may be carried out by the so-called PCR (see reference below) or PCR-like methods. PCR-like will be understood to designate all the methods using direct or indirect reproductions of the nucleic acid sequences, or in which the labeling systems have been amplified; these techniques are well known, in general they relate to the amplification of DNA by polymerase; when the original samples is an RNA, it is advisable to carry out a reverse transcription beforehand; a great number of methods allowing this amplification currently exists, for example the so-called NASBA and TMA methods which are well known to persons skilled in the art.

Table B gives the sequences of the PCR primers which make it possible to amplify the exons as well as the temperatures for the PCR reactions.

A general methodology for amplification of the sequences will be described in the examples.

Test for Point Mutations

In addition to the direct sequencing of the mutation, various methods may be used. The techniques will be briefly cited:

1) test for "Single Strand Conformation Polymorphisms" (SSCP) (see reference below) or denaturing gradient gel electrophoresis (DGGE).
2) the methods based on a cleavage of the mismatched regions (enzymatic cleavage by S1 nuclease, chemical cleavage by various compounds such as piperidine or osmium tetroxide, and the like.
3) heteroduplex detection by electrophoresis,
4) methods based on the use in hybrication of allele-specific oligonucleotide (ASO) probes.

Other well known methods based on hybrication techniques can be used.

Test for Deletion, Inversion or Duplication Type Rearrangements

Other well known methods based on the techniques of hybridization with the aid of genomic probes, of cDNA probes, of oligonucleotide probes, of riboprobes, of so-called capture probes or of so-called detection probes, may be used for the test for this type of rearrangement.

Another diagnostic approach which can be used when DNA from several subjects of the same family is available is based on the method of linkage analysis which makes it possible to calculate the risk which a subject belonging to a linked family has of being a carrier or otherwise of the diseased gene. This analysis may be carried out with polymorphic markers situated in the immediate vicinity of the gene, or intragenic polymorphic markers.

It is important to recall that in the CADASIL families, the existence of mutations in the Notch3 gene corresponds to mutations which change amino acids which are essential for the function of the protein for which it encodes.

Moreover, in the examples, the situations of the mutations currently detected are indicated, but it is possible that other mutations exist in the Notch3 gene which have not yet been detected but which should lead to the same types of risks from the pathological point of view.

In any case, the mutated Notch3 proteins may exhibit an antigenicity which is different from that of the natural protein.

It is therefore possible to carry out a diagnosis or a prognosis of a susceptibility to neurological, in particular cerebrovascular, disorders of the CADASIL type and disorders linked to the Notch3 receptor, by detecting the product of the mutated gene for Notch3; this type of detection can be carried out, for example, with the aid of monoclonal or polyclonal antibodies. Under these conditions, it is possible to detect and assay the abnormal product of the Notch3 gene by well known methods, RIA or ELISA for example; these technologies being known, they will not be further developed beforehand in the text which follows. Antibodies directed against the normal protein could also be used if the deposit present in the arteries of the skin corresponded to the Notch3 protein or to one of its cleavage products.

The present invention also relates to the labeled monoclonal or polyclonal antibodies corresponding to all or part of the mutated proteins so as to serve as imaging agent in vivo or ex vivo on biological samples.

Thus, it appears that the granular masses present in the basals of the vascular smooth muscle cells are due to an accumulation of the abnormal protein and the test for this protein with the aid of antibodies, either in biopsies or in vivo, is of a diagnostic interest.

Methods Based on the Detection of the Product of the Gene

The mutations of the Notch3 gene may be responsible for various modifications of the product of this gene, modifications which can be used for a diagnostic approach. Briefly, the protein may be truncated, reduced in size or absent; its properties, in particular its antigenicity, may be modified. All these modifications may be used in a diagnostic approach using several well known methods based on the use of mono- or polyclonal antibodies which recognize the normal protein or mutated variants, and this using the study of protein extracts or of tissue sections (for example skin biopsies), or studies carried out in vivo (imaging with the aid of antibodies coupled to a molecule which is detectable in PET-scan type imaging, and the like).

The polyclonal or monoclonal antibodies may be obtained by immunological reaction of a human or animal organism with an immunogenic agent consisting of a protein or a polypeptide capable of being obtained from prokaryotic or eukaryotic cells transformed by a vector as described above. Preferably, the immunogenic agent consists of a specific polypeptide of the mutated form of the Notch protein whose sequence is chosen from the polypeptide sequences comprising at least one mutation chosen from the mutations corresponding to FIG. 3 or to Table C.

The present invention finally relates to therapeutic compositions containing, as active ingredient, a compound with a pro-Notch3 activity, especially as described above, as well as therapeutic compositions containing, as active ingredient, a compound with an anti-Notch3 activity.

Figure 4:
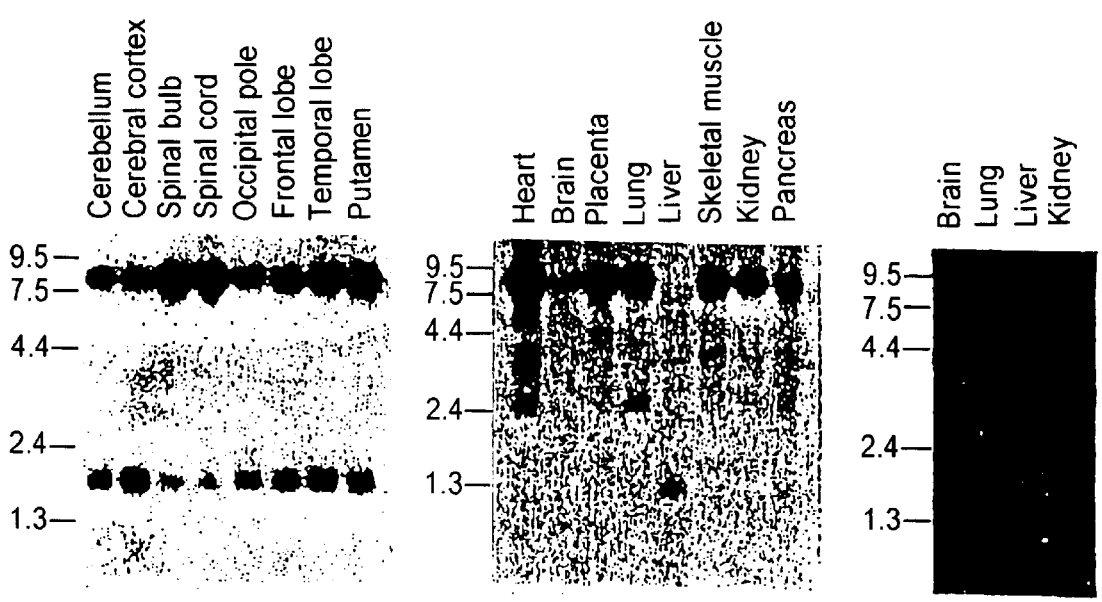

Other characteristics and advantages of the present invention will appear on reading the examples below, with reference to the accompanying drawings in which:

FIG. 1 reproduces the cDNA sequence (SEQ ID NO:1) of human Notch3 as well as the corresponding protein sequence (SEQ ID NO:2). Panels 1A–1H present the sequences in consecutive order, with the sequences on each panel following directly from the preceding panel;

FIG. 2 represents the general structure of the product of the Notch3 gene as well as the mutations which were detected by aligning the human cDNA clones with mouse Notch3, A—mouse Notch3 gene with its 34 EGF domains, 3 Notch/Lin12 repeats and 6 cdc10 repeats, as well as the transmembrane domain, B—at the bottom, 8 of the human cDNAs with the identifications corresponding to FIG. 1, at the top, the alignment of some genomic sequences with the cDNA of at least 29 exons, the origins of the various fragments appear at the bottom of FIG. 4; the various clones are available commercially or through libraries;

the clones 261623; 153875; 149693 are available from the IMAGE consortium;

the clone C-32b03 is available from GENEXPRESS (Généthon, Evry, France);

the clones p28–20; CNA-20 are available from CLONTECH;

FIG. 3 schematically represents the situation and the nature of the mutations involved in CADASIL;

FIG. 4 represents a "Northern blot" analysis, the Northern blots containing 2 µg per line of human poly (A$^+$) DNA, from left to right:

of various brain tissues, of various adult organs, of various fetal organs;

they are hybridized with p28–20, a Notch3 human 1.45 kb cDNA probe; a 7.5 to 9.5 kb transcript is detected in all the tissues, both adult and fetal, with the exception of the liver, the transcript is weakly expressed in the brain tissue in the middle and on the right; on the contrary, on the left, not only are transcripts of all the tissues observed, but also the presence of a transcript of between 2.4 and 1.3 kb whose presence has never been mentioned and which may be of a very high importance is observed.

EXAMPLE 1

Scheme for the Isolation and Analysis of the Notch3 Gene

Following the remarks and the analysis which were summarized at the beginning of the description as regards the location of the gene, murine cDNA probes were used to isolate the cDNA for the human Notch3 gene, and then genomic clones whose sequences could be aligned with it and with the murine cDNA sequences.

Additional information on the sequences were obtained from a cDNA fragment (884Na4) obtained by cDNA selection on YAC (884g1) and from two genomic fragments (J431NH and J432NH) which were obtained by subcloning of BAC 13J4 NotI-HindIII fragments.

In the screening of the (dBest) data bank with all the sequences, it has been possible to identify additional clones (IMAGE clones, Genexpress).

The coding sequence of the human Notch3 gene, which is highly homologous to the corresponding murine gene, is represented in FIG. 1.

Table A schematically represents the structure of the gene, specifying the sequence and the position of the exon-intron junctions.

In this table, the first exon corresponds to a sequence whose 5' end was not completely cloned, likewise for exon 33.

It should be noted that alternative cDNAs may exist which correspond to the known phenomenon of alternative splicing.

This sequence contains 34 EGF domains, 3 Notch/lin12 repeats, as well as 3 cdc10 ankyrin-like repeats. The human and murine proteins exhibit 90.5% identity on the sequence currently available. A 1.45 kb partial human cDNA probe containing the EGF-like domains reveals a ubiquitous transcript in the fetal tissues, as well as in the human adult tissues whose size of between 7.5 and 9.5 kb is similar to the murine transcript (FIG. 4).

This probe reveals another transcript in certain subregions of the brain whose size is estimated at between 1.3 and 2.4 kb (FIG. 4).

EXAMPLE 2

Study of the Mutations

In order to study the extent of the mutations in the Notch3 gene on CADASIL, the possible presence of a substantial genomic DNA rearrangement was first studied using various combinations of enzymes and of Notch3 probes.

No drastic rearrangement could be detected in the CADASIL patients, that is why point mutations were then tested for.

Thus, the mutations of the total coding sequence of the Notch3 gene in the genomic DNA were studied using a combination of SSCP method and heteroduplex analysis in 51 CADASIL patients with no family relationship. 28 of them belong to families for which the evidence for a relationship with chromosome 19 has been demonstrated and 33 exhibit ultrastructural lesions of the wall of the arterioles of the skin (presence of osmiophilic granular deposits in the basal membrane of the vascular smooth muscle cells).

All the splicing junctions, except 3, were analyzed. In addition, direct sequencing of the PCR products of exon 4 and its splicing sites was carried out on all the patients.

Impairments which were compatible with corresponding mutations were found in 42 patients (82%), said mutations not being observed in any of the 200 control chromosomes. For 26 patients, it was possible to analyze one or more which were related, affected or otherwise, and in each case it was established that the mutation segregated with the CADASIL phenotype. There are 29 different mutations, of which 20 are described for the first time. They include 24 missense mutations which appear in 40 patients, which mutations should replace (16) one amino acid with an additional or mutated cysteine (8) one of the 6 cysteine residues, which are the key elements of the EGF domains.

Two of the mutations at the 5' splicing site in the latter two patients should normally affect the splicing of exon 4. The last three mutations are missense mutations which appear in 3 patients simultaneously with the mutations described above.

Patient 21 carries 2 distinct mutations which change an arginine to cysteine at codon 141 in EGF 3 and which changes a conserved glycine to alanine at codon 288 in EGF 7. This patient's pedigree was not available; it was not therefore possible to study the cosegregation of these two mutations.

Patient 29 carries a first mutation in EGF 4 which changes an arginine 182 to cysteine and a second which changes a highly conserved alanine 1852 to threonine in the cdc10 domain. These two mutations segregated with the disease.

The last patient 55 is a carrier of two distinct mutations in the EGF domains, which change a cysteine (224) to a tryptophan and a nonconserved leucine (497) to a serine residue.

Although the latter three missense mutations are not detected in the 200 control chromosomes, they may involve rare polymorphisms given the presence also of missense mutations which mutate or create cysteine residues.

It should be noted that most of these 26 mutations having a pathogenic effect lie exclusively in the EGF parts. 41% of these mutations (11 out of 26) appearing in 25 patients are situated in exon 4 and 65% (17 out of 26) lie in the first 6 EGF domains (see in particular FIG. 3.

FIG. 3 allows the detection to characterize the main mutations detected, the nomenclature chosen indicates the position of the mutation as well as the corresponding modifications of the protein.

As was indicated above, the fact that a Notch gene is involved in neurological disorders in adults appears completely surprising since Notch is mainly known to be involved during development in drosophila. None of the CADASIL families studied up until now exhibits developmental abnormalities.

EXAMPLE 3

Detection of the Mutations in Patients by the SSCP Method

The oligonucleotides used as primers were synthesized from intron-exon joining sequences (Table B) so as to amplify genomic fragments of about 200 bp. The sequences of the PCR primers are given below (Table A).

The analyses can be carried out using DNA extracted from blood samples or any other tissue.

The amplification reactions are carried out in a final volume of 25 $\mu$l containing 100 ng of genomic DNA, 0.5 $\mu$m of each primer, 150 $\mu$g of a mixture of 4dNTPs, Taq polymerase 1XPCR from Cetus, 1 U Taq polymerase (BRL), 1.5 $\mu$Ci $\alpha$dCTP labeled with P33 according to a protocol comprising 30 identical cycles (94° C., 15 s; 65° C., 15 s; 72° C., 15 s).

For some of the primers, an "annealing" temperature of 70° C. should be used, as indicated in Table A.

The PCR products are denatured in 50% formamide and separated by electrophoresis in a 6% nondenaturing polyarylamide gel.

After autoradiography, the SSCP bands obtained in the patients are compared with those of healthy controls in search of abnormal variants. Their analysis can be used as a diagnostic approach. These variants can then be sequenced if necessary.

TABLE A

Exon-intron structure of the Notch3 gene (sequences and positions of the exon-intron junctions)

| Splice Acceptor Site Intron/Exon | | Exon (Size) | Position | Splice Donor Site Exon/Intron | |
|---|---|---|---|---|---|
| | | 1 | 1–196 | CTGCAG/gtgagggc laAlaAl | (SEQ ID NO:3) |
| cccacacag/CCCCCC aProPr | (SEQ ID NO:4) | 2 (79) | 197–275 | CTGCCT/gtgagtgcc aCysLe | (SEQ ID NO:5) |
| gcccacag/GTGCCC uCysPr | (SEQ ID NO:6) | 3 (143) | 276–418 | TCCGAG/gtgagagg heArgG | (SEQ ID NO:7) |
| ccctccag/GCCCTG lyProA | (SEQ ID NO:8) | 4 (339) | 419–757 | TTCCTG/gtgagtga euProG | (SEQ ID NO:9) |
| cttgttag/GGTTTG lyPheG | (SEQ ID NO:10) | 5 (123) | 758–880 | GGACAG/gtgggcac rpThrG | (SEQ ID NO:11) |
| tgccacag/GCCAGT lyGlnP | (SEQ ID NO:12) | 6 (234) | 881–1114 | AGACTG/gtgagtgg ysThrG | (SEQ ID NO:13) |
| cttcccag/GCCTCC lyLeuL | (SEQ ID NO:14) | 7 (156) | 1115–1270 | CTATCG/gtgagggg erIleG | (SEQ ID NO:15) |
| tccggcag/GCGCCA lyAlaA | (SEQ ID NO:16) | 8 (187) | 1271–1456 | TGGCCA/gtgggtgg etAlaG | (SEQ ID NO:17) |
| tgccccag/GCTTCA lyPheT | (SEQ ID NO:18) | 9 (114) | 1457–1570 | CCTCGG/gtgaggac roSerG | (SEQ ID NO:19) |
| caccccag/GCTTCA lyPheS | (SEQ ID NO:20) | 10 (114) | 1571–1684 | CCGAGG/gtgaggcg laGluG | (SEQ ID NO:21) |
| ccccacag/GCTTTG lyPheG | (SEQ ID NO:22) | 11 (234) | 1685–1918 | CCACAG/gtgggacc hrThrG | (SEQ ID NO:23) |
| gcccctag/GTGTGA lyValA | (SEQ ID NO:24) | 12 (111) | 1919–2029 | TCACAG/gtgggcaa heThrG | (SEQ ID NO:25) |
| ctccccag/GGCCCC lyProL | (SEQ ID NO:26) | 13 (193) | 2030–2222 | TGGCGG/gtgagggc oGlyGl | (SEQ ID NO:27) |
| cctgccag/GTTCCG yPheAr | (SEQ ID NO:28) | 14 (152) | 2223–2374 | TCCAGG/gtgtgtac alGlnG | (SEQ ID NO:29) |
| cccaacag/GACGTC lyArgG | (SEQ ID NO:30) | 15 (114) | 2375–2488 | GGCAAG/gtatgccac rpGlnG | (SEQ ID NO:31) |
| taccccag/GCCCAC lyProA | (SEQ ID NO:32) | 16 (156) | 2489–2644 | ACCCCA/gtgagtgca spProA | (SEQ ID NO:33) |
| gtccgcag/ACCCAT snProC | (SEQ ID NO:34) | 17 (226) | 2645–2870 | CCCCAG/gtgggcgg rProSe | (SEQ ID NO:35) |
| cgctccag/CTCCTG rSerCy | (SEQ ID NO:36) | 18 (202) | 2871–3072 | TGCCAG/gtgggtgg CysGln | (SEQ ID NO:37) |
| ccctccag/ACGCTG ThrLeu | (SEQ ID NO:38) | 19 (148) | 3073–3220 | AGATCG/gtgagtgg lnIleG | (SEQ ID NO:39) |
| ctttgcag/GGGTGC lyValA | (SEQ ID NO:40) | 20 (185) | 3221–3405 | TGTGAG/gtaagggg CysGlu | (SEQ ID NO:41) |
| cactgaag/TGTCTT CysLeu | (SEQ ID NO:42) | 21 (133) | 3406–3538 | CGCTGG/gtatgcca hrLeuG | (SEQ ID NO:43) |

TABLE A-continued

Exon-intron structure of the Notch3 gene (sequences and positions of the exon-intron junctions)

| Splice Acceptor Site Intron/Exon | Exon (Size) | Position | Splice Donor Site Exon/Intron |
|---|---|---|---|
| tcccccag/GGGTGC (SEQ ID NO:44) lyValL | 22 (258) | 3539–3796 | TCTCAG/gttaacct (SEQ ID NO:45) heSerG |
| tcgctcag/GTCCTC (SEQ ID NO:46) lyProA | 23 (119) | 3797–3915 | GCCCAG/gtaggtgtg (SEQ ID NO:47) AlaGln |
| gaccccag/CCGTTC (SEQ ID NO:48) ProPhe | 24 (566) | 3916–4481 | TTGCAA/gtgagccc (SEQ ID NO:49) rCysAs |
| cccaccag/CCCGGT (SEQ ID NO:50) nProVa | 25 (333) | 4482–4814 | GATCGG/gtgagtgac (SEQ ID NO:51) lIleG |
| tccctgcag/CTCGGT (SEQ ID NO:52) ySerVal | 26 (155) | 4815–4969 | TGCGCG/gtgcggcc (SEQ ID NO:53) alArgG |
| tgctcttag/GGGGAGC (SEQ ID NO:54) lyGluP | 27 (223) | 4970–5192 | CATGAA/gtgagaac (SEQ ID NO:55) yMetLy |
| tccgccag/GAACAT (SEQ ID NO:56) sAsnMe | 28 (85) | 5193–5277 | CTAAAG/gtactgcc (SEQ ID NO:57) LeuLys |
| cccctccag/GTAGAG (SEQ ID NO:58) ValGlu | 29 (162) | 5278–5440 | GCCCAG/gtcagtgac (SEQ ID NO:59) lyProA |
| ccctgcag/ATGGCT (SEQ ID NO:60) spGlyP | 30 (305) | 5441–5745 | TTCCAG/gtgagata (SEQ ID NO:61) PheGln |
| tgtcctag/ATTCTC (SEQ ID NO:62) IleLeu | 31 (148) | 5746–5893 | AGCTTG/gtaggttg (SEQ ID NO:63) luLeuG |
| ccctccag/GGAAAT (SEQ ID NO:64) lyLysS | 32 (99) | 5894–5992 | AGCAAG/gtgagccc (SEQ ID NO:65) SerLys |
| cccccag/GAGGAG (SEQ ID NO:66) GluGlu | 33 | 5993– | |

TABLE B

Sequences of the primers used for the screening of the mutations of the Notch3 gene

| Exon | Size | Domain | Primers | | PCR product size | |
|---|---|---|---|---|---|---|
| 1 | | Signal peptide | E0F | AAGGAGGGAGGAGGGGAG | 125 | (SEQ ID NO:66) |
| | | | E0R | TGGGGGTTCTTGCACTCC* | | (SEQ ID NO:67) |
| | | | E0F | AAGGAGGGAGGAGGGGAG | 163 | (SEQ ID NO:68) |
| | | | E0RBIS | GGTTCCTGCCTCCCATGA* | | (SEQ ID NO:69) |
| 2 | 79 | EGF1 | E1F | TCCTCCACCTTCCTTCAC* | 148 | (SEQ ID NO:70) |
| | | | E1R | ACACACAGGGCCCACTGGT* | | (SEQ ID NO:71) |
| 3 | 143 | EGF 1–2 | N1 F | TGTGCTGCCCAACCAAGCCA* | 224 | (SEQ ID NO:72) |
| | | | N1 R | ACTGACCACACCCCCGACTA* | | (SEQ ID NO:73) |
| 4 | 339 | EGF 2–5 | N2A F | TAGTCGGGGTGTGGTCAGT* | 192 | (SEQ ID NO:74) |
| | | | N2A R | TCATCCACGTCGCTTCGGCA* | | (SEQ ID NO:75) |
| | | | CNA F | ATGGACGCTTCCTCTGCTC | 167 | (SEQ ID NO:76) |
| | | | CNA R | ACATAGTGGCCCTGTGTAGC | | (SEQ ID NO:77) |
| | | | CNA F | ATGGACGCTTCCTCTGCTCC | 295 | (SEQ ID NO:78) |
| | | | N3AR | CCTCTGACTCTCCTGAGTAG* | | (SEQ ID NO:79) |
| 5 | 123 | EGF 5–6 | N23Fbis | TGACCATCCTTGCCCCCTT* | 241 | (SEQ ID NO:80) |
| | | | N23 R | CTGGCCTGTGGCACACAGAT* | | (SEQ ID NO:81) |
| 6 | 234 | EGF6–8 | N13A F | TGGACTGCTGCATCTGTGTG* | 191 | (SEQ ID NO:82) |
| | | | N13A R | ACACGCCTGTGGCACAGTCA | | (SEQ ID NO:83) |
| | | | N13B F | GAGCTGCAGTCAGAATATCG | 145 | (SEQ ID NO:84) |
| | | | N13B R | ATCCATGGCTCCCTGCAGAG* | | (SEQ ID NO:85) |
| 7 | 156 | EGF 8–10 | N24 F | CAGAGCAGGAAGATCTGCCT* | 229 | (SEQ ID NO:86) |
| | | | N24 R | CATTCACAGACGACGGAGCT* | | (SEQ ID NO:87) |
| 8 | 187 | EGF 10–11 | N3 F | ATCGCACTCCATCCGGCA* | 212 | (SEQ ID NO:88) |
| | | | N3 R | ACCCACCTGCCATACAGA* | | (SEQ ID NO:89) |
| 9 | 114 | EGF 11–12 | N25A F | CGTTCACACCATAGGGTAGC* | 215 | (SEQ ID NO:90) |
| | | | N25A R | CCCCTTCCCAGACATGTCTT | | (SEQ ID NO:91) |
| 10 | 114 | EGF 12–13 | N25BF | CTTGTCGGACTGTCATTGG | 195 | (SEQ ID NO:92) |
| | | | N25BR | GTGTACTGCTCTCACCCTT* | | (SEQ ID NO:93) |
| 11 | 234 | EGF 13–15 | N4AF | ATTGGTCCGAGGCCTCACTT* | 213 | (SEQ ID NO:94) |
| | | | N4AR | ACCTGGCTCTCGCAGCGTGT | | (SEQ ID NO:95) |
| | | | N4B R | CCATTCCCAACCCCTCTGTG | 199 | (SEQ ID NO:96) |
| | | | N4B F | TGCCTGTGCTCCTGGCTACA* | | (SEQ ID NO:97) |
| 12 | 111 | EGF 15–16 | N5 F | TGGCCACTCCATGCCATGTT* | 166 | (SEQ ID NO:98) |
| | | | N5 R | TCTCATGGCAGCCACTTGCC* | | (SEQ ID NO:99) |
| 13 | 193 | EGF 16–18 | N14 F | ATGAGTGTGCTTCCAGCCCA* | 258 | (SEQ ID NO:100) |
| | | | N14 R | GCAGTGTCTGAGGCTGAGAA* | | (SEQ ID NO:101) |

TABLE B-continued

Sequences of the primers used for the screening of the mutations of the Notch3 gene

| Exon | Size | Domain | Primers | | PCR product size | |
|---|---|---|---|---|---|---|
| 14 | 152 | EGF 18–19 | N6 F | TCCCTGGCCTGACTACCTTC* | 207 | (SEQ ID NO:102) |
| | | | N6 R | CTGCAGAGGGAAGGTGAGGT* | | (SEQ ID NO:103) |
| 15 | 114 | EGF 19–20 | N26BF | AAGGCTATCCTGCTTCC* | 183 | (SEQ ID NO:104) |
| | | | N26BR | GAGGAGGAGGGAAGAGAA* | | (SEQ ID NO:105) |
| 16 | 156 | EGF 20 22 | S13FBIS | AGGATGTGGACGAGTGTGCT | 195 | (SEQ ID NO:106) |
| | | | N26CR | GCTTAATGACTGTGTTCC* | | (SEQ ID NO:107) |
| 17 | 226 | EGF 22–24 | N15A F | TCAGACTGGGCTAATGGGGG* | 257 | (SEQ ID NO:108) |
| | | | N15A R | TCGCAGTGGAAGCCTCCGTA | | (SEQ ID NO:109) |
| | | | N15B F | GATGTGGATGAGTGCCTGAG | 166 | (SEQ ID NO:110) |
| | | | N15B R | GTCCTGCTCTTCAAGCAGA* | | (SEQ ID NO:111) |
| 18 | 202 | EGF 24–25 | N27F | GATCCTCCCTCCCACTCCTT* | 256 | (SEQ ID NO:112) |
| | | | N27R | AGGTCCCCAGTAACTCCA* | | (SEQ ID NO:113) |
| 19 | 148 | EGF 25–27 | N22F | ACTGACTCTAAGTGCTTCCC* | 240 | (SEQ ID NO:114) |
| | | | N22R | AGCAGGAGGTACGTGCATGA* | | (SEQ ID NO:115) |
| 20 | 185 | EGF 27–28 | N7 F | TGTTCCTGTGCCACTCTCCT* | 249 | (SEQ ID NO:116) |
| | | | N7 R | ACCTCCTCTTCCCTCTCCT* | | (SEQ ID NO:117) |
| 21 | 133 | EGF 28–29 | N8 F | TCTGTGTCCCACTAAGCTGA* | 237 | (SEQ ID NO:118) |
| | | | N8 R | CAAGAGGAAATGAAGACAGC* | | (SEQ ID NO:119) |
| 22 | 258 | EGF 29–31 | N9A F | TTCCTCTTGACCACCCCTCG* | 217 | (SEQ ID NO:120) |
| | | | N9A R | TGGCAGGCACCTGAGCGACA | | (SEQ ID NO:121) |
| | | | N9B F | CAGGATACACTGGTTTGCGC | 209 | (SEQ ID NO:122) |
| | | | N9B R | TGCCACGTTATGGATCAGCC* | | (SEQ ID NO:123) |
| 23 | 119 | EGF 31–32 | N10 F | GATCTACATGCTCCCGCTCG* | 178 | (SEQ ID NO:124) |
| | | | N10 R | TACTCCTCCTCCATAGGCCG* | | (SEQ ID NO:125) |
| 24 | 566 | EGF 32–34 | N16AFTR | CGTTCTGGGGTCCGCGTT | 249 | (SEQ ID NO:126) |
| | | Lin12 N1-3 | N16DR | AAGCGCAGCGGAAGAAGGGC | | (SEQ ID NO:127) |
| | | | N16FF | GCCCTTCTTCCGCTGCGCTT | 230 | (SEQ ID NO:128) |
| | | | N16FR | ACTGCAGCGCCTCGCATTGC | | (SEQ ID NO:129) |
| | | | N16GF | CTGCGACCGCGAGTGCAACA | 239 | (SEQ ID NO:130) |
| | | | N16HR | ATAGACAGACGGATCGAT* | | (SEQ ID NO:131) |
| 25 | 331 | Lin12 N3 | N21CF | CTCTCTGCCTCACCCTT* | 207 | (SEQ ID NO:132) |
| | | | N21CR | GCTGGAACGCAGTAGCT | | (SEQ ID NO:133) |
| | | | N21DF | TGCTCACAGTGCTGCTG | 223 | (SEQ ID NO:134) |
| | | | N21DR | CACGGCTTTTCCAGGTG* | | (SEQ ID NO:135) |
| 26 | 155 | | N34F | TTTGAGCCCTCTGGTCC* | 306 | (SEQ ID NO:136) |
| | | | N34R | AAGAGCAGGAAGCAGAG* | | (SEQ ID NO:137) |
| 27 | 222 | TM | N28Fbis | TCCCTCTGCTTCCTGCTCTT* | 291 | (SEQ ID NO:138) |
| | | | N28R | TCACAAGGTCCCCGTAGTCA* | | (SEQ ID NO:139) |
| 28 | 85 | | J5N3 F | CTCACATCCCCTCTTCCCAT* | 203 | (SEQ ID NO:140) |
| | | | J5N3 R | ATCACGCCCATCATCCACTG* | | (SEQ ID NO:141) |
| 29 | 163 | Cdc10 N1 | L24bisf | CAGCACCAAAGGGTG* | 241 | (SEQ ID NO:142) |
| | | | L24bisR | CATCCCTTTGGGAGG* | | (SEQ ID NO:143) |
| 30 | 305 | Cdc10 N1–3 | N17AF | ATGGCTTCACCCCGCTAATG | 176 | (SEQ ID NO:144) |
| | | | N17AR | AGCCAGGTGCAAAGCAGTCT | | (SEQ ID NO:145) |
| | | | N17BF | TCAGCTTGGGGCACGGACTG | 165 | (SEQ ID NO:146) |
| | | | N17BR | GCATCGGCTGTGACAGCTGT | | (SEQ ID NO:147) |
| 31 | 148 | Cdc10 N4–5 | N26FBIS | TGTTCCTGCCATGACCCCT* | 239 | (SEQ ID NO:148) |
| | | | N26RBIS | CAGGTGACACTAACCCAGTC* | | (SEQ ID NO:149) |
| 32 | 98 | Cdc10 N5–6 | N31F | TCCTGACCTCTCTCCCCTTC* | 178 | (SEQ ID NO:150) |
| | | | N31R | AATGGCGCTGTGCCACTGCT* | | (SEQ ID NO:151) |
| 33 | | Cdc10 N6 | N32AF | GCTACTGTTAGCTGGGGTTT* | 214 | (SEQ ID NO:152) |
| | | NLS | N32AR | TGATCCAGCAAGCGCACGAT | | (SEQ ID NO:153) |
| | | PEST | | | | |
| | | | N32EFTER | TCACCGACCACCTGGACA | 425 | (SEQ ID NO:154) |
| | | | N32DR | ACCAAGCTGTGCCAGAGA | | (SEQ ID NO:155) |
| | | | N32DF | TCCAAGAAGAGCAGGAGG | 246 | (SEQ ID NO:156) |
| | | | N32DR | ACCAAGCTGTGCCAGAGA | | (SEQ ID NO:157) |
| | | | N32B F | CAGTGTCTCTGGCACAGCTT | 248 | (SEQ ID NO:158) |
| | | | N32BR | TCCTGGGACTGCCAGGTAA | | (SEQ ID NO:159) |
| | | | N32CF | AGCTGCTCAACCCAGGGA | 229 | (SEQ ID NO:160) |
| | | | N32CR | GTGGATTCGGACCAGTCT | | (SEQ ID NO:161) |
| | | | N32GF | GAATCCCCTGAGCACT | 235 | (SEQ ID NO:162) |
| | | | N32GR | CTAAGAACTGACGAGC | | (SEQ ID NO:163) |

*intronic primers

TABLE C

Notch3 mutations in CADASIL patients

| Patient | Evidence of linkage | SMC lesions | Notch3 nt[a] | Notch3 mutation | Effect | Exon | Domain | Segregation |
|---|---|---|---|---|---|---|---|---|
| 52* | nd | nd | 224 | TGT-->TAT | $C_{49}$-->Y* | N2 | EGF1 | nd |
| 56 | nd | + | 291 | TGG-->TGT | $W_{71}$-->C | N3 | EGF1 | nd |
| 11 | + | nd | 406 | CGT-->TGT | $R_{110}$-->C | N3 | EGF2 | + |
| 3 | + | + | 419(-2) | AG-->GG | abnormal splicing of exon 4? | N4 | | + |
| 39 | nd | + | 419(-2) | AG-->CG | abnormal splicing of exon 4? | N4 | | nd |
| 10 | + | + | 475 | CGC-->TGC | $R_{133}$-->C | N4 | EGF3 | + |
| 20 | nd | + | 475 | CGC-->TGC | $R_{133}$-->C | N4 | EGF3 | nd |
| 46 | + | nd | 475 | CGC-->TGC | $R_{133}$-->C | N4 | EGF3 | + |
| 6 | + | nd | 499 | CGC-->TGC | $R_{141}$-->C | N4 | EGF3 | + |
| 12 | + | + | 499 | CGC-->TGC | $R_{141}$-->C | N4 | EGF3 | + |
| 19 | + | nd | 499 | CGC-->TGC | $R_{141}$-->C | N4 | EGF3 | + |
| 21* | nd | + | 499 | CGC-->TGC | $R_{141}$-->C | N4 | EGF3 | nd |
|  |  |  | 941 | GGC-->GCG | $G_{288}$-->A* | N5 | EGF7 | nd |
| 38 | + | nd | 499 | CGC-->TGC | $R_{141}$-->C | N4 | EGF3 | + |
| 49 | + | + | 499 | CGC-->TGC | $R_{141}$-->C | N4 | EGF3 | + |
| 26 | + | + | 514 | TGC-->CGC | $C_{146}$-->R | N4 | EGF3 | + |
| 4 | + | + | 535 | CGC-->TGC | $R_{153}$-->C | N4 | EGF3 | + |
| 50 | nd | + | 535 | CGC-->TGC | $R_{153}$-->C | N4 | EGF3 | + |
| 9* | + | + | 583 | CGC-->TGC | $R_{169}$-->C* | N4 | EGF4 | + |
| 15* | + | nd | 583 | CGC-->TGC | $R_{169}$-->C* | N4 | EGF4 | + |
| 24 | + | nd | 583 | CGC-->TGC | $R_{169}$-->C | N4 | EGF4 | + |
| 36* | nd | + | 583 | CGC-->TGC | $R_{169}$-->C* | N4 | EGF4 | nd |
| 48 | nd | + | 583 | CGC-->TGC | $R_{169}$-->C | N4 | EGF4 | nd |
| 1 | + | nd | 589 | GGT-->TGT | $G_{171}$-->C | N4 | EGF4 | + |
| 45* | + | + | 622 | CGC-->TGC | $R_{182}$-->C* | N4 | EGF4 | + |
| 47* | nd | + | 622 | CGC-->TGC | $R_{182}$-->C* | N4 | EGF4 | nd |
| 29* | + | + | 622 | CGC-->TGC | $R_{182}$-->C | N4 | EGF4 | + |
|  |  |  | 5632 | GCT-->ACT | $A_{1852}$-->T* | N30 | cdc10 | + |
| 41 | nd | + | 631 | TGT-->CGT | $C_{185}$-->R | N4 | EGF4 | nd |
| 57 | nd | + | 712 | TGC-->AGC | $C_{212}$-->S | N4 | EGF5 | nd |
| 8 | + | nd | 742 | TGT-->GGT | $C_{222}$-->G | N4 | EGF5 | + |
| 55 | nd | nd | 749 | TGT-->TAT | $C_{224}$-->Y | N4 | EGF5 | + |
|  |  |  | 1568 | TCG-->TTG | $S_{497}$-->L | N9 | EGF12 | - |
| 14 | + | + | 851 | TAT-->TGT | $Y_{258}$-->C | N5 | EGF6 | + |
| 54* | nd | + | 1703 | TGT-->TAT | $C_{542}$-->Y* | N11 | EGF13 | nd |
| 17* | + | + | 1750 | CGC-->TGC | $R_{558}$-->C* | N11 | EGF14 | + |
| 18* | + | + | 1750 | CGC-->TGC | $R_{558}$-->C* | N11 | EGF14 | + |
| 31* | nd | + | 1810 | CGC-->TGC | $R_{578}$-->C* | N11 | EGF14 | + |
| 43 | nd | nd | 2260 | CGC-->TGC | $R_{728}$-->C | N14 | EGF18 | nd |
| 25 | + | + | 3031 | CGC-->TGC | $R_{985}$-->C | N18 | EGF25 | + |
| 42 | nd | + | 3031 | CGC-->TGC | $R_{985}$-->C | N18 | EGF25 | nd |
| 7 | + | nd | 3094 | CGC-->TGC | $R_{1006}$-->C | N19 | EGF26 | + |
| 35 | nd | nd | 3169 | CGC-->TGC | $R_{1031}$-->C | N19 | EGF26 | + |
| 33 | nd | nd | 3769 | CGC-->TGT | $R_{1231}$-->C | N22 | EGF31 | nd |
| 58* | nd | + | 3859 | TGC-->CGC | $C_{1261}$-->R* | N23 | EGF32 | nd |

*patient and mutation previously reported[7]
SMC: smooth muscle cell

REFERENCES FOR THE VARIOUS METHODS CITED ABOVE

Polymerase Chain Reaction (PCR)
Saiki et al., Science 239, p. 487, 1988+reference manual.
SSCP
Orita et al., Proc. Natl. Acad. Sci. USA, 86, p. 2766–2770, 1989.
Techniques for Detection of Mutations Based on the Demonstration of Mismatches
  chemical cleavage
  enzymatic cleavage (S1 nuclease)
  heteroduplex
  Allele Specific Oligonucleotide probes (ASO)

References
Cotton et al., Proc. Natl. Acad. Sci. USA, 85, 4397, 1988
Sherk et al., Proc. Natl. Acad. Sci. USA, 72, 989, 1975
Cariello, Hum. Genet., 42, 726, 1988

Cloning Vectors and Basic Molecular Biology Techniques
Current protocols in molecular biology, Eds F. M. Ausubel, R. Brent, R. E. Kingston, D. D. Moore, S. G. Seldman, J. A. Smith and K. Struhl, Published by Green Publishing Associates and Wiley Interscience, 1st edition 1987, John Wiley and sons
Molecular cloning. A laboratory manual, J. Sambrook, EF Fritsch and T. Mariatis, 2nd edition, 1989, Cold Spring Harbor Laboratory Press

What is claimed is:

1. An isolated cDNA encoding a polypeptide comprising the amino acid sequence of SEQ ID NO:2.

2. The isolated cDNA of claim 1, wherein the cDNA comprises the nucleic acid sequence of SEQ ID NO:1.

3. A vector for the cloning or expression, in an appropriate host cell, of a nucleic acid, said vector comprising an isolated cDNA according to claim 1.

4. The vector according to claim 3, which comprises elements allowing the expression of said sequence in said host cell.

5. The vector according to claim 3, which is an autonomously replicating vector.

6. The vector according to claim 3, which is a chromosomal integrating vector.

7. The vector according to claim 3, which is a viral vector.

8. The vector according to claim 7, wherein the vector is prepared based on an adenovirus, a retrovirus, a poxvirus, or a herpesvirus.

9. A cell transformed with a vector according to claim 3.

10. The cell according to claim 9, which is a prokaryotic cell.

11. The cell according to claim 9, which is a eukaryotic cell.

12. A method of producing a polypeptide encoded by an isolated cDNA according to claim 1, said method comprising:

culturing a cell that is transformed with a vector comprising an isolated cDNA according to claim 1, and recovering said polypeptide.

* * * * *

UNITED STATES PATENT AND TRADEMARK OFFICE
CERTIFICATE OF CORRECTION

PATENT NO. : 6,537,775 B1
DATED : March 25, 2003
INVENTOR(S) : Elisabeth Tournier-Lasserve et al.

It is certified that error appears in the above-identified patent and that said Letters Patent is hereby corrected as shown below:

<u>Title page,</u>
Item [73], "Assignee: Institut National de la Sante et de la Recherche (INSERM)" should read -- Assignee: Institut National de la Sante et de la Recherche Medicale (INSERM) --.

Signed and Sealed this

Twelfth Day of August, 2003

JAMES E. ROGAN
*Director of the United States Patent and Trademark Office*